United States Patent

Ichikawa et al.

[11] Patent Number: 5,866,724
[45] Date of Patent: Feb. 2, 1999

[54] POSITIVE RESIST COMPOSITION AND PHOTOSENSITIZERS

[75] Inventors: Koji Ichikawa; Haruyoshi Osaki; Hiroki Inoue, all of Osaka, Japan

[73] Assignee: Sumitomo Chemical Company, Limited, Osaka, Japan

[21] Appl. No.: 733,166

[22] Filed: Oct. 17, 1996

[30] Foreign Application Priority Data

| Oct. 18, 1995 | [JP] | Japan | 7-270294 |
|---|---|---|---|
| Oct. 18, 1995 | [JP] | Japan | 7-270297 |
| Oct. 18, 1995 | [JP] | Japan | 7-270305 |
| Apr. 23, 1996 | [JP] | Japan | 8-101224 |
| Apr. 23, 1996 | [JP] | Japan | 8-101225 |
| Apr. 23, 1996 | [JP] | Japan | 8-101226 |
| Apr. 24, 1996 | [JP] | Japan | 8-102485 |
| Jun. 20, 1996 | [JP] | Japan | 8-159710 |

[51] Int. Cl.⁶ ............... C07C 39/15; C07C 309/71; C07C 309/76
[52] U.S. Cl. ............... 568/720; 534/557; 568/718
[58] Field of Search ............... 534/557; 568/718, 568/720, 744

[56] References Cited

U.S. PATENT DOCUMENTS

| 5,153,096 | 10/1992 | Uenishi et al. | 430/192 |
|---|---|---|---|
| 5,407,778 | 4/1995 | Uetani et al. | 430/192 |
| 5,407,779 | 4/1995 | Uetani et al. | 430/192 |

FOREIGN PATENT DOCUMENTS

| 0573056 | 12/1993 | European Pat. Off. |
|---|---|---|
| 5-204148 | 8/1993 | Japan . |
| 91/03448 | 3/1991 | WIPO . |
| 96/20430 | 4/1996 | WIPO . |

OTHER PUBLICATIONS

Database WPI, Patent Abstract AN 95–257302/JP–A–07 159 990 (1995) (Abstract).
Database WPI, Chemical Abstracts 123:213221 (1995) (Abstract).
Database WPI, Chemical Abstracts 125:181328/WO 96–20430 A1 (Abstract).

Primary Examiner—Fiona T. Powers
Attorney, Agent, or Firm—Birch, Stewart Kolasch & Birch, LLP

[57] ABSTRACT

A positive photoresist compositions comprising, as a photosensitizer, a quinonediazide sulfonic acid ester of a phenol compound represented by the following formula (I):

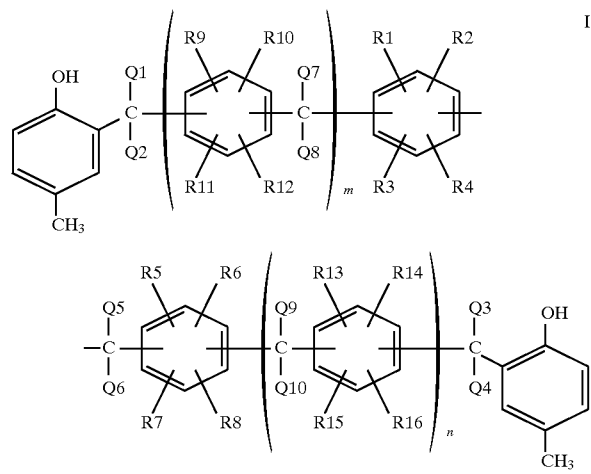

wherein $Q^1, Q^2, Q^3, Q^4, Q^5, Q^6, Q^7, Q^8, Q^9$ and $Q^{10}$ independently represent hydrogen, alkyl having 1–6 carbon atoms or phenyl, or $Q^1$ and $Q^2$, $Q^3$ and $Q^4$, $Q^5$ and $Q^6$, $Q^7$ and $Q^8$, or $Q^9$ and $Q^{10}$ may form a cycloalkane ring having 6 or less carbon atoms together with a carbon atoms to which they are connected, $R^1, R^2, R^3, R^4, R^5, R^6, R^7, R^8, R^9, R^{10}, R^{11}, R^{12}, R^{13}, R^{14}, R^{15}$ and $R^{16}$ independently represent hydrogen, hydroxyl, alkyl having 1–6 carbon atoms or phenyl; and m and n independently represent a number of 0 or 1;
and an alkali soluble resin;

and a quinonediazide sulfonic acid ester of a phenol compound of formula (I).

6 Claims, No Drawings

POSITIVE RESIST COMPOSITION AND PHOTOSENSITIZERS

The present invention relates to photosensitive resin compositions, particularly positive photoresist compositions which give a positive pattern by irradiation with a radiation such as near ultra-violet ray and deep ultra-violet ray including excimer laser.

It has been generally known that quinonediazide sulfonic acid esters of compounds having a phenolic hydroxyl group are used as photosensitizers in photosensitive resin composition for minute processing for semiconductors. These compositions are used as positive resists utilizing the fact that when a composition comprising a compound having a quinonediazide group and a novolak resin is applied on a substrate, and is then irradiated with a light of 300–500 nm, the quinonediazide group is decomposed to form a carboxyl group, allowing to change the composition from an alkali-insoluble state to an alkali-soluble state. Since such positive resists are characterized in that they are excellent in resolution as compared with negative resists, they found utilization in producing various kinds of integrated circuits for semiconductors.

In recent years, the integrated circuits in the semiconductor industries have gone on increasing minuteness with a progress of the level of integration and now formation of a pattern in submicron order is demanded. Especially, the lithographic process occupies an important position in the production of integrated circuits and a more excellent resolution (high γ-value) is required for the positive resists.

Many combinations of ingredients have been proposed for resist materials containing a quinonediazide compound and a novolak resin. For example, JP-A-1-189644 (corr. to U.S. Pat. No. 5,153,096) has disclosed a use of quinonediazide sulfonic acid esters of triphenylmethane compounds having at least two phenolic hydroxyl groups as photosensitizers. When these known sensitizers were used, however, there was a limit in improvement of the γ-value as the resist for the ultra minute processing currently used in the production of ultrahigh integrated circuits or for so-called submicron lithography. Therefore, various researches have been carried out in order to improve properties as the resist such as sensitivity, resolution, heat resistance and the like. For example, JP-A-6-167805 (corr. to EP-A-573,056) has disclosed a use of quinonediazide sulfonic acid esters of compounds having four or more phenol nuclei as photosensitizers.

An object of the present invention is to provide photosensitive resin compositions, particularly positive photoresist compositions which are well balanced among various properties as the resist such as high sensitivity, high resolution, high heat resistance, good profile, good forcus latitude, little development residue and the like, using such compounds.

Another object of the present invention is to provide novel phenol compounds which can be used as a photosensitiser for photosensitive resin compositions such as positive photoresist.

As the result of researches, the inventors have found that positive photoresist compositions which are more balanced among various properties as the resists compared to known positive photoresist compositions can be obtained by using specific phenol compounds having groups derived from para-cresol at their both ends. Thus the present invention have been completed.

The present invention provides a positive photoresist compositions comprising, as a photosensitizer, a quinonediazide sulfonic acid ester of a phenol compound represented by the following formula (I):

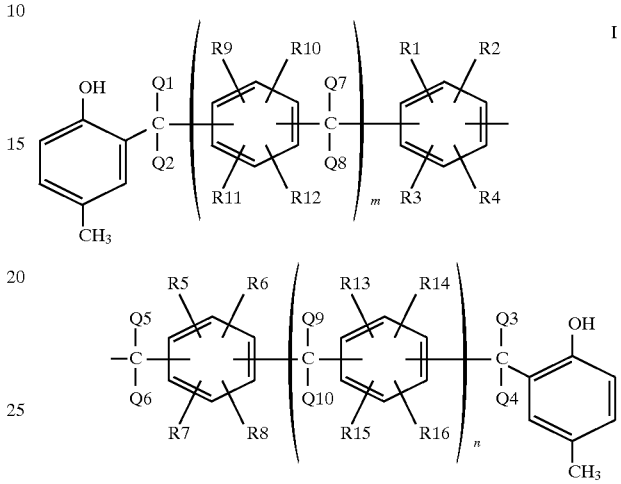

wherein $Q^1, Q^2, Q^3, Q^4, Q^5, Q^6, Q^7, Q^8, Q^9$ and $Q^{10}$ independently represent hydrogen, alkyl having 1–6 carbon atoms or phenyl, or $Q^1$ and $Q^2$, $Q^3$ and $Q^4$, $Q^5$ and $Q^6$, $Q^7$ and $Q^8$, or $Q^9$ and $Q^{10}$, may form a cycloalkane ring having 6 or less carbon atoms together with a carbon atoms to which they are connected, $R^1, R^2, R^3, R^4, R^5, R^6, R^7, R^8, R^9, R^{10}, R^{11}, R^{12}, R^{13}, R^{14}, R^{15}$ and $R^{16}$ independently represent hydrogen, hydroxyl, alkyl having 1–6 carbon atoms or phenyl; and m and n independently represent a number of 0 or 1;

and an alkali soluble resin.

The present invention also provides phenol compounds represented by the following formulae VII, X, XI, XII, XIII or XIV:

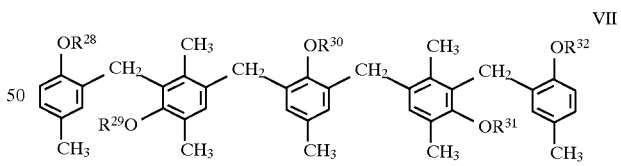

wherein $R^{28}, R^{29}, R^{30}, R^{31}$ and $R^{32}$ independently represent hydrogen, 1,2-naphthoquinonediazide-4-sulfonyl or 1,2-naphthoquinonediazide-5-sulfonyl;

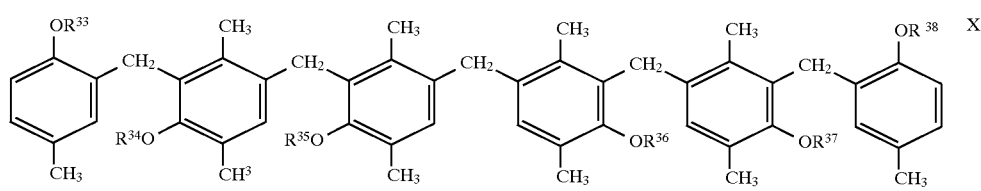

wherein
$R^{33}$, $R^{34}$, $R^{35}$, $R^{36}$, $R^{37}$ and $R^{38}$ independently represent hydrogen, 1,2-naphthoquinonediazide-4-sulfonyl or 1,2-naphthoquinonediazide-5-sulfonyl;

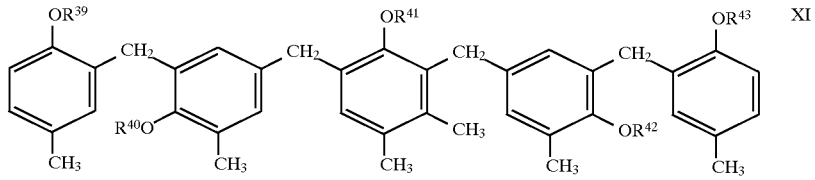

wherein
$R^{39}$, $R^{40}$, $R^{41}$, $R^{42}$ and $R^{43}$ independently represent hydrogen, 1,2-naphthoquinonediazide-4-sulfonyl or 1,2-naphthoquinonediazide-5-sulfonyl;

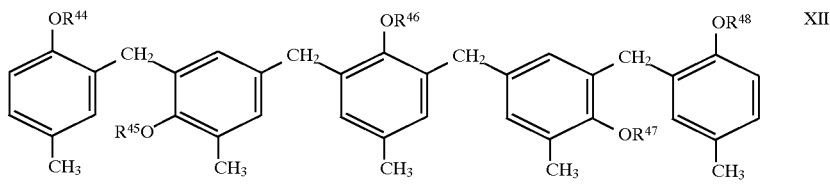

wherein
$R^{44}$, $R^{45}$, $R^{46}$, $R^{47}$ and $R^{48}$ independently represent hydrogen, 1,2-naphthoquinonediazide-4-sulfonyl or 1,2-naphthoquinonediazide-5-sulfonyl;

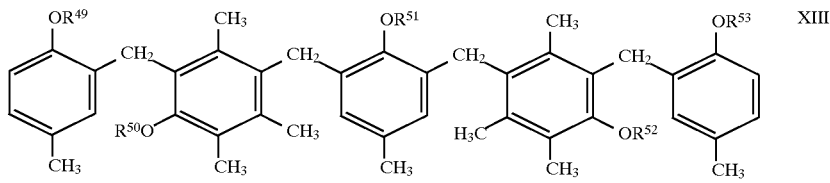

wherein
$R^{49}$, $R^{50}$, $R^{51}$, $R^{52}$ and $R^{53}$ independently represent hydrogen, 1,2-naphthoquinonediazide-4-sulfonyl or 1,2-naphthoquinonediazide-5-sulfonyl; and

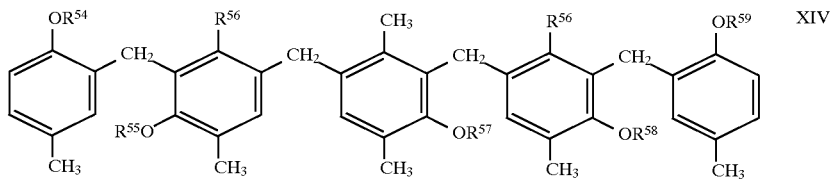

wherein $R^{56}$ represents hydrogen or methyl and $R^{54}$, $R^{55}$, $R^{57}$, $R^{58}$ and $R^{59}$ independently represent hydrogen, 1,2-naphthoquinonediazide-4-sulfonyl or 1,2-naphthoquinonediazide-5-sulfonyl. In the above-mentioned formula VII, X, XI, XII, XIII or XIV, 1,2-naphthoquinonediazide-4-sulfonyl is represented by the following formula VIII and 1,2-naphthoquinonediazide-5-sulfonyl is represented by the following formula IX.

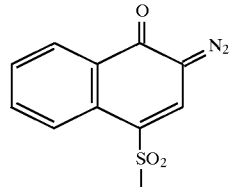

VIII

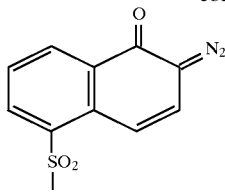

The compound represented by the above-mentioned formulae VII, X, XI, XII, XIII or XIV which has at least one naphthoquinone sulfonyl group in the molecule is included in the phenol compound of formula (I) and can be used as a photosensitizer for the positive resist composition of the present invention.

Among the phenol compounds of formula (I), those in which at least one of $R^1$, $R^2$, $R^3$ and $R^4$ is hydroxyl, at least one of $R^{5\ 1}$, $R^6$, $R^7$ and $R^8$ is hydroxyl, at least one of $R^9$, $R^{10}$, $R^{11}$ and $R^{12}$ is hydroxyl, and at least one of $R^{13}$, $R^{14}$, $R^{15}$ and $R^{16}$ is hydroxyl are preferably used for the starting material of the quinonediazide sulfonic acid ester. Among the preferred phenol compounds of formula (I), more preferred are those in which remaining $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$, i.e. those groups which are not hydroxyl, are hydrogen and alkyl. As the alkyl, methyl is particularly preferred.

Also, among the phenol compounds of formula (I), those in which $Q^1$, $Q^2$, $Q^3$ and $Q^4$ are hydrogen are preferably used for the starting material of the quinonediazide sulfonic acid ester.

The phenol compounds of formula (I) can be produced, for example, by reacting dihydric alcohol represented by the following formula (II):

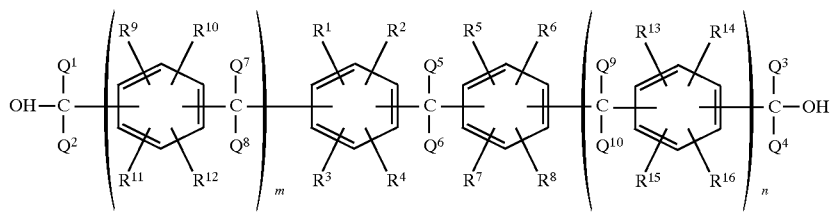

wherein
$Q^1$, $Q^2$, $Q^3$, $Q^4$, $Q^5$, $Q^6$, $Q^7$, $Q^8$, $Q^9$, $Q^{10}$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$,
m and n have same meanings as defined above,
with para-cresol in the presence of an acid catalyst such as para-toluene sulfonic acid, hydrochloric acid and sulfuric acid.

The dihydric alcohol of formula (II) can be produced, for example, by reacting a compound represented by the following formula (III):

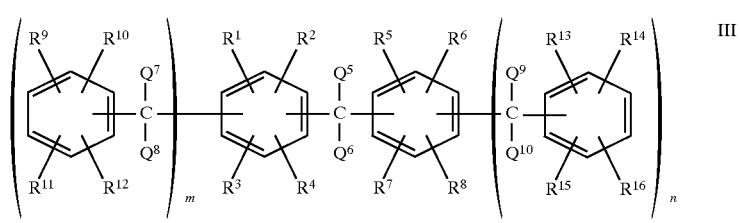

wherein $Q^5$, $Q^6$, $Q^7$, $Q^8$, $Q^9$, $Q^{10}$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, m and n have same meanings as defined above, with an aldehyde or a ketone. Some of the compounds of formula (III) are on the market. Therefore, it is easily available. Also, it can be obtained by a reaction in which, at first, a mono-benzene nucleus compound is reacted with an aldehyde or a ketone, then, the resulting dinuclei compound is reacted with a mono-benzene nucleus compound and an aldehyde or a ketone and, then, reaction between the resulting polynuclei compound and a mono-benzene nucleus compound is repeated.

Also, the phenol compounds of formula (I) can be produced by a condensation reaction of a compound of above-mentioned formula (III) with a compound represented by the following formula (IV) and a compound represented by the following formula (v):

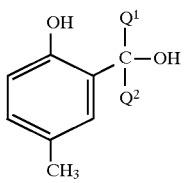

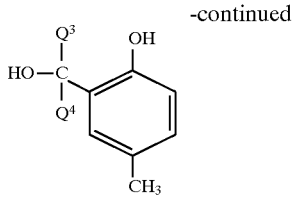

in the presence of an acid catalyst such as para-toluene sulfonic acid and sulfuric acid.

Further, the phenol compounds of formula (I) can also be produced by reacting a compound of above-mentioned formula (III) with para-cresol and an aldehyde or a ketone.

As mentioned above, phenol compounds of formula (I) in which $Q^1$, $Q^2$, $Q^3$ and $Q^4$ are hydrogen are preferably used. The preferred phenol compounds of formula (I) can be produced by reacting a compound of above-mentioned formula (III) with formaldehyde in the presence of an alkaline catalyst such as sodium hydroxide to obtain a dihydric alcohol of formula (II) in which $Q^1$, $Q^2$, $Q^3$ and $Q^4$ are hydrogen, i.e. dimethylol compound, followed by reacting the dihydric alcohol of formula (II) thus obtained with para-cresol in the presence of an acid catalyst.

The phenol compound of formula VII, X, XI, XII, XIII or XIV wherein $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{57}$, $R^{58}$ and $R^{59}$ are hydrogen can be produced, for example, by reacting para-cresol with 2,6-bis(4-hydroxy-3-hydroxymethyl-2,5-dimethylbenzyl)-4-methylphenol, 4,4'-methylenebis[2-(4-hydroxy-3-hydroxymethyl-2,5-dimethylbenzyl)-3,6-dimethylphenol], 2,6-bis(4-hydroxy-3-hydroxymethyl-5-methylbenzyl)-3,4-dimethylphenol, 2,6-bis(4-hydroxy-3-hydroxymethyl-5-methylbenzyl)-4-methylphenol, 2,6-bis(4-hydroxy-3-hydroxymethyl-2,5,6-trimethylbenzyl)-4-methylphenol, or a compound represented by the following formula XV:

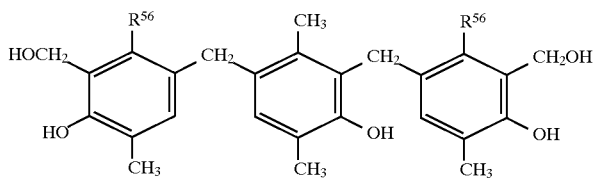

XV wherein $R^{56}$ is same as defined above, respectively.

The dimethylol compounds, 2,6-bis(4-hydroxy-3-hydroxymethyl-2,5-dimethylbenzyl)-4-methylphenol, 4,4'-methylenebis[2-(4-hydroxy-3-hydroxymethyl-2,5-dimethylbenzyl)-3,6-dimethylphenol], 2,6-bis(4-hydroxy-3-hydroxymethyl-5-methylbenzyl)-3,4-dimethylphenol, 2,6-bis(4-hydroxy-3-hydroxymethyl-5-methylbenzyl)-4-methylphenol, 2,6-bis(4-hydroxy-3-hydroxymethyl-2,5,6-trimethylbenzyl)-4-methylphenol and a compound of formula XV, (Hereinafter, these six dimethylol compounds are referred to as "Dimethylol compound A") can be obtained, for example, by reacting 2,6-bis(4-hydroxy-2,5-dimethylbenzyl)-4-methylphenol, 4,4'-methylenebis[2-(4-hydroxy-2,5-dimethylbenzyl)-3,6-dimethylphenol], 2,6-bis(4-hydroxy-3-methylbenzyl)-3,4-dimethylphenol, 2,6-bis(4-hydroxy-3-methylbenzyl)-4-methylphenol, 2,6-bis(4-hydroxy-2,3,6-trimethylbenzyl)-4-methylphenol, or a compound represented by the following formula XVI:

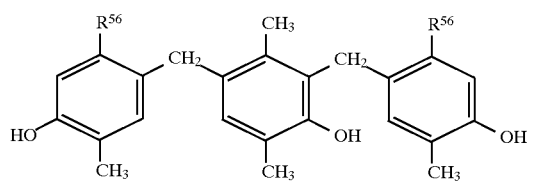

XVI wherein $R^{56}$ is same as defined above, respectively, (Hereinafter, these six compounds are referred to as "Starting compound B") with formaldehyde in the presence of an alkaline catalyst.

2,6-Bis(4-hydroxy-2,5-dimethylbenzyl)-4-methylphenol can be obtained, for example, by a condensation reaction of 2,6-bis(hydroxymethyl)-4-methylphenol and 2,5-xylenol. 2,6-Bis(hydroxymethyl)-4-methylphenol can be obtained by reacting para-cresol with formaldehyde.

4,4'-Methylenebis[2-(4-hydroxy-2,5-dimethylbenzyl)-3,6-dimethylphenol], which is described in JP-A-6-167805(= U.S. Pat. No. 5,407,779), can be obtained, for example, by a condensation reaction of 4,4'-methylenebis(2-hydroxymethyl-3,6-dimethylphenol) and 2,5-xylenol. 4,4'-Methylenebis (2-hydroxymethyl-3,6-dimethylphenol) can be obtained by reacting 2,5-xylenol with formaldehyde.

2,6-Bis(4-hydroxy-3-methylbenzyl)-3,4-dimethylphenol can be obtained, for example, by a condensation reaction of 2,6-bis(hydroxymethyl)-3,4-dimethylphenol and ortho-cresol. 2,6-Bis(hydroxymethyl)-3,4-dimethylphenol can be obtained by reacting 3,4-xylenol with formaldehyde.

2,6-Bis(4-hydroxy-3-methylbenzyl)-4-methylphenol can be obtained, for example, by a condensation reaction of 2,6-bis(hydroxymethyl)-4-methylphenol and ortho-cresol.

2,6-Bis(4-hydroxy-2,3,6-trimethylbenzyl)-4-methylphenol can be obtained, for example, by a condensation reaction of 2,6-bis(hydroxymethyl)-4-methylphenol and 2,3,5-trimethylphenol.

A compound of formula XVI can be obtained, for example, by a condensation reaction of 2,4-bis (hydroxymethyl)-3,6-dimethylphenol with ortho-cresol or 2,5-xylenol. 2,4-Bis(hydroxymethyl)-3,6-dimethylphenol can be obtained by reacting 2,5-xylenol with formaldehyde.

In the reaction of Starting compound B with formaldehyde to produce Dimethylol compound A, the molar ratio of Starting compound B and formaldehyde is usually 1:2–10, preferably 1:4–8. For the production of 2,6-bis(4-hydroxy-3-hydroxymethyl-2,5-dimethylbenzyl)-4-methylphenol, the ratio of 1:5–6 is more preferred.

This reaction is carried out in the presence of an alkaline catalyst. Although, either an inorganic base or an organic base can be used, an inorganic base such as sodium hydroxide, potassium hydroxide, sodium carbonate and potassium carbonate are preferred as the alkaline catalyst, Particularly, sodium hydroxide is preferred. The amount of the alkaline catalyst is preferably 0.5–5 mol, more preferably 1–4 mol, further more preferably 2–3 mol, for the production of 2,6-bis(4-hydroxy-3-hydroxymethyl-2,5-dimethylbenzyl)-4-methylphenol; and preferably 0.5–8 mol, more preferably 1–5 mol, for the production of 4,4'-methylenebis[2-(4-hydroxy-3-hydroxymethyl-2,5-dimethylbenzyl)-3,6-dimethylphenol], 2,6-bis(4-hydroxy-3-hydroxymethyl-5-methylbenzyl)-3,4-dimethylphenol, 2,6-bis(4-hydroxy- 3-hydroxymethyl-5-methylbenzyl)-4-methylphenol, 2,6-bis(4-hydroxy-3-hydroxymethyl-2,5,6-trimethylbenzyl)-4-methylphenol and a compound of formula XV, per 1 mol of Starting compound B.

This reaction is usually carried out in an solvent. As the solvent, a polar solvent such as tetrahydrofuran, dioxane, water and methanol are preferred and, particularly, a mixed solvent of tetrahydrofuran and water is preferred. The amount of the reaction solvent is preferably 1–10 parts by weight, more preferably 3–6 parts by weight, further more preferably 4–5 parts by weight, for the production of 2,6-bis(4-hydroxy-3-hydroxymethyl-2,5-dimethylbenzyl)-4-methylphenol; and is preferably 2–30 parts by weight, for the production of 4,4'-methylenebis[2-(4-hydroxy-3-hydroxymethyl-2,5-dimethylbenzyl)-3,6-dimethylphenol], 2,6-bis(4-hydroxy-3-hydroxymethyl-5-methylbenzyl)-3,4-dimethylphenol, 2,6-bis(4-hydroxy-3-hydroxymethyl-5-methylbenzyl)4-methylphenol, 2,6-bis(4-hydroxy-3-hydroxymethyl-2,5,6-trimethylbenzyl)-4-methylphenol and a compound of formula XV, per 1 part by weight of Starting compound B.

When a mixed solvent of tetrahydrofuran and water is used, the amount of tetrahydrofuran is preferably 0.05–1 parts by weight, more preferably 0.1–0.5 parts by weight, particularly preferably 0.1–0.2 parts by weight, per 1 part by weight of water.

This reaction is usually carried out within a temperature range of 10°–60° C. For the production of 2,6-bis(4-hydroxy-3-hydroxymethyl-2,5-dimethylbenzyl)-4-methylphenol, this reaction is preferably carried out at 30°–50° C., particularly preferably 35°–45° C.

For this reaction, adding formaldehyde to a mixture of Starting compound B, an alkaline catalyst and a solvent over a period of time is preferred in order to avoid generation of too much heat. Preferably, as the formaldehyde, an aqueous solution of formaldehyde is used.

For the production of 2,6-bis(4-hydroxy-3-hydroxymethyl-2,5-dimethylbenzyl)-4-methylphenol, for example, the reaction mass is neutralized with acid to precipitated the reaction product and it is filtered to obtain the reaction product of high purity in high yield.

In the reaction of Dimethylol A with para-cresol, para-cresol is used in an amount generally of 2–50 moles, preferably of 4–20 moles, per 1 mole of Dimethylol compound A. For the reaction of 2,6-bis(4-hydroxy-3-hydroxymethyl-2,5-dimethylbenzyl)-4-methylphenol with para-cresol, the amount of 8–20 moles per 1 mole of Dimethylol compound A is more preferred.

It is preferred that an acid catalyst is present in this reaction. The acid catalyst may be either an inorganic acid such as hydrochloric acid and sulfuric acid or an organic acid such as formic acid, acetic acid, propionic acid and paratoluene sulfonic acid. Among them, a mineral acid such as hydrochloric acid and sulfuric acid and paratoluene sulfonic acid is preferred, and among them, paratoluene sulfonic acid is particularly preferred. The acid catalyst is used in an amount usually of 1 equivalent or less and preferably within a range of 0.1–0.5 equivalent based on Dimethylol compound A.

The reaction is preferably carried out in a solvent. Aromatic solvents, water, alcohols and the like can be used as the reaction solvent for the reaction of 4,4'-methylenebis[2-(4-hydroxy-3-hydroxymethyl-2,5-dimethylbenzyl)-3,6-dimethylphenol], 2,6-bis(4-hydroxy-3-hydroxymethyl-5-methylbenzyl)-3,4-dimethylphenol, 2,6-bis(4-hydroxy-3-hydroxymethyl-5-methylbenzyl)-4-methylphenol, 2,6-bis(4-hydroxy-3-hydroxymethyl-2,5,6-trimethylbenzyl)-4-methylphenol or a compound of formula XV with para-cresol. For the reaction of 2,6-bis(4-hydroxy-3-hydroxymethyl-2,5-dimethylbenzyl)-4-methylphenol with para-cresol, aromatic solvents, particularly aromatic hydrocarbon solvents, are preferred. Examples of the alcohols include lower alcohols such as methanol, ethanol, propanol and butanol, among which methanol is preferred. Examples of the aromatic hydrocarbon solvents include benzene, toluene and xylene, among which toluene is preferred. The reaction solvent is used in an amount generally within a range of 0.5- to 5-fold weight, preferably 1- to 3-fold weight, based on the total amount of Dimethylol compound A and p-cresol.

The reaction is carried out at a temperature usually within a range of 10° C. to the boiling temperature, preferably within a range of 15°–60° C., more preferably within a range of 40°–60° C. The reaction is usually carried out under the atmospheric pressure.

The reaction product crystallizes as the reaction proceeds when the reaction is carried out around room temperature. When the reaction is carried out at a higher temperature, the reaction product crystallizes upon cooling to room temperature after completion of the reaction. A crude product can be obtained by isolating the crystals and may be subjected to an optional purification step. For example, the compound can be purified by crystallization from an aromatic solvent or by repetition thereof as desired. The crystallizing solvent may be the same as or different from that used in the reaction.

Phenol compounds of formula (I), reaction product of the above-mentioned reactions, can be isolated by crystallization from an aromatic solvent such as benzene, toluene and xylene, preferably toluene.

It is preferred to decrease metal content in the phenol compounds of formula (I) by dissolving the crude product in a solvent having a solubility of 9 g/100 g or less in water, then washing the resulting solution with water and separating. A solubility of 9 g/100 g or less means that the maximum amount of the solvent soluble in 100 g of water at 20° C. is 9 g or less. Further, it is preferred to use a solvent in which the phenol compounds of formula (I) has a solubility of 1 g/100 g or more at a temperature of 20° C. Such solvent includes, for example, acetic acid esters such as ethyl acetate, n-butyl acetate and isoamyl acetate, ketones such as methyl isobutyl ketone and 2-heptanone, among which ethyl acetate is preferred.

The phenol compounds of formula (I) thus obtained can be converted into a quinonediazide sulfonic acid ester, which can be used as a photosensitizer. In the esterification, various kinds of sulfonic acid derivatives having a 1,2-quinonediazide structure such as 1,2-benzoquinonediazide-4- or -5-sulfonyl halide and 1,2-naphthoquinonediazide-4- or -5-sulfonyl halide can be used as an esterifying agent. Among them, 1,2-naphthoquinonediazide-4- or -5-sulfonyl halide is preferred. The halogen in the sulfonyl halide may be, for example, chlorine, bromine and the like, among which chlorine is usually preferred. Hence, as the sulfonic acid derivatives, 1,2-naphthoquinonediazide-4- or -5-sulfonyl chloride is more preferred as an esterifying agent. Also, a mixture of 1,2-naphthoquinonediazide-4-sulfonyl halide and 1,2-naphthoquinonediazide-5-sulfonyl halide can be used. In the esterification reaction, quinonediazide sulfonyl halide is used in a molar ratio usually of 1.2 per 1 mole of the phenol compounds of formula (I).

The reaction is usually conducted in the presence of a dehydrohalogenating agent. The dehydrohalogenating agent includes generally basic compounds, for example, inorganic bases such as sodium carbonate and sodium hydrogen carbonate and amines such as ethylamine, ethanolamine, diethylamine, diethanolamine, triethylamine, N,N-dimethylaniline and N,N-diethylaniline. The dehydrohalogenating agent is used in a molar ratio usually of 1.05–1.5, preferably of 1.05–1.2 and more preferably of 1.1–1.2, per 1 mole of 1,2-naphthoquinonediazide-4- or -5-sulfonyl halide.

The esterification reaction is usually conducted in a solvent. The solvent for the reaction includes ethers, lactones, aliphatic ketones and the like and is preferably selected from dioxolane, 1,4-dioxane, tetrahydrofuran, γ-butyrolactone, acetone and 2-heptanone. These can be used alone or in combination of two or more. Among them, 1,4-dioxane is preferred. The solvent for reaction is used in an amount usually within a range of 2- to 6-fold weight, preferably 3- to 5- fold weight and more preferably 4- to 5-fold weight based on the total amount of the phenol compounds of formula (I) and quinonediazide sulfonyl halide.

The esterification reaction well proceeds under an ordinary pressure and around an ordinary temperature but generally conducted at a temperature of 20°–30° C. for 2–10 hours.

After completion of the reaction, the objective ester crystallizes out when the reaction mixture is neutralized with an acid such as acetic acid, followed by filtering off solid substance and mixing of the filtrate with a diluted aqueous acid solution, for example, an aqueous acetic acid solution of about 1% by weight. The ester can be isolated from the resulting mixture by filtration, washing and drying.

By the esterification reaction, usually, a mixture of two or more of the quinonediazide sulfonyl esters of a phenol compound of the formula (I) wherein a part of the phenolic hydroxyl groups is converted into quinonediazide sulfonyl and all of the phenolic hydroxyl groups are converted into quinonediazide sulfonyl is produced, depending on the molar ratio of 1,2-naphthoquinone-diazide sulfonyl halide used. This mixture can usually be used as it is for a photosensitizer. A mixture of the quinonediazide sulfonyl esters produced from two or more kind of a phenol compound of the formula (I) can also be used.

The esterified compounds may advantageously be used for photosensitizers sensitive to radiation such as ultraviolet rays, far ultraviolet rays (including excimer lasers etc.) and the like.

For a photosensitizer, if desired, the esterified compounds may be used in combination with a quinonediazide sulfonyl esters of another phenol compound. Examples of the quinonediazide sulfonyl esters of another phenol compound includes a compound described in JP-A-5-204148, a compound described in JP-A-5-323597(=EP-A-570,884), a compound described in JP-A-6-167805(=EP-A-573,056), and a compound represented by the following formula (VI):

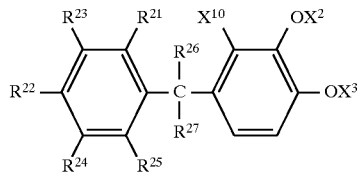

wherein one of $R^{21}$ and $R^{22}$ represents—$OX^4$; the other one of $R^{21}$ and $R^{22}$, $R^{23}$, $R^{24}$ and $R^{25}$ independently represent hydrogen, alkyl having 6 or less carbon atoms, cycloalkyl having 6 or less carbon atoms, alkenyl having 6 or less carbon atoms, alkoxy having 6 or less carbon atoms or halogen; $R^{26}$ and $R^{27}$ independently represent hydrogen, alkyl having 6 or less carbon atoms, alkenyl having 6 or less carbon atoms, or $R^{26}$ and $R^{27}$ form a cycloalkane ring having 6 or less carbon atoms together with a carbon atom to which they are connected; and $X^1$, $X^2$, $X^3$ and $X^4$ independently represent hydrogen or quinonediazide sulfonyl provided that at least one of $X^1$, $X^2$, $X^3$ and $X^4$ is quinonediazide sulfonyl (This compound is described in Japanese patent application No. 7-58826).

In the present invention, the photosensitizer, including other quinonediazide sulfonic acid esters if used, is preferably contained in an amount within a range of 10–50% by weight based on the total solid amount in the resist composition.

The alkali-soluble novolak resins as a constituent of the positive resist composition are resins obtained by condensing a compound having at least one phenolic hydroxyl group with an aldehyde in the presence of an acid catalyst. They are not limited in their kind and may be any one usable in the field of resist. The phenol compounds as the starting material for the novolak resins include, for example, meta-cresol, para-cresol, ortho-cresol, 2,5-xylenol, 3,5-xylenol, 3,4-xylenol, 2,3,5-trimethylphenol, 2-t-butyl-5-methylphenol, t-butylhydroquinone and the like. The aldehydes as the other starting material for the novolak resins include formaldehyde, acetaldehyde, benzaldehyde, glyoxal, salicylaldehyde and the like. Particularly, formaldehyde is industrially mass-produced in the form of a 37% aqueous solution and is suitable for use.

The novolak resins are obtained by condensing one, two or more of the phenol compounds with one, two or more of the aldehydes in the presence of an acid catalyst. As the acid catalyst, an organic acid, an inorganic acid, a salt of bivalent metal and the like may be used. Specific examples include oxalic acid, acetic acid, para-toluene sulfonic acid, hydrochloric acid, sulfuric acid, phosphoric acid, zinc acetate and the like. The condensation reaction can be conducted according to the ordinary method, for example, at a temperature within a range of 60°–120° C. for about 2–30 hours. The reaction may be carried out without diluent or in a suitable solvent.

The obtained novolak resin is preferably treated, for example by fractionation, to form a resin which has a ratio of an area in a pattern of gel-permeation chromatography (GPC, using a UV254 nm detector ) for a portion having a molecular weight converted into polystyrene of 900 or less being 25% or less based on the total area in the pattern except an area in the pattern for unreacted phenol compound, for purposes such as minimization of undeveloped residue of the resist. Further, it is more preferred to adjust the ratio of area for the portion having a molecular weight converted into polystyrene of 900 or less to 20% or less.

Methods for the fractionation include a method in which the novolak resin is dissolved in a good solvent, for example, an alcohol such as methanol and ethanol, a ketone such as acetone, methyl ethyl ketone, and methyl isobutyl ketone, an ethylene glycol ether such as ethyl cellosolve, an ethylene glycol ether ester such as ethyl cellosolve acetate or a cyclic ether such as tetrahydrofuran, and then the solution is poured into water to precipitate high molecular weight components; and a method in which the above solution is mixed with a poor solvent such as pentane, hexane and heptane, followed by phase separation.

It is also effective to add an alkali-soluble phenol compound having a molecular weight of 900 or less to the novolak resin which is made rich in high molecular weight components by a fractionation treatment such as those mentioned above. The alkali-soluble phenol compounds having a molecular weight of 900 or less preferably have two or more phenolic hydroxyl groups in the molecular structure and include, for example, those described in JP-A-2-275955 (EP-A-358,871) or JP-A-2-2560. The alkali-soluble phenol compound having a molecular weight of 900 or less, when used, is preferably contained in an amount within a range of 3–40% by weight based on the total solid amount in the resist composition.

Preparation of a resist solution is carried out by mixing and dissolving a photosensitizer, an alkali soluble resin and further, if necessary, an alkali-soluble phenol compound having a molecular weight of 900 or less in a solvent. As the solvent, one which has a suitable drying rate and which gives a uniform and flat membrane after evaporation is preferred. Such solvents include glycol esters such as propylene glycol monomethyl ether acetate, ethyl cellosolve acetate and methyl cellosolve acetate, esters such as ethyl pyruvate, n-amyl acetate and ethyl lactate, ketones such as 2-heptanone, cyclic esters such as γ-butyrolactone, and further solvents described in JP-A-2-220056, those described in JP-A-4-362645, those described in JP-A-4-367863 and the like. These solvents can be used singly or in combination of two or more.

The obtained resist solution or photosensitive resin composition may further contain a small amount of resin or dye as required.

EXAMPLES

The present invention will be described in more detail with Examples which should not be construed as a limitation to the scope of the present invention. In the Examples, % and parts used for showing contained or added amount are weight based unless otherwise specified.

Synthesis Example 1

(1) Production of 4,4'-methylenebis[2-(2-hydroxy-5-methylbenzyl)-3,6-dimethylphenol](hereinafter referred to as compound 1)

Into a 500 ml three-necked flask were charged 144.16 g of para-cresol, 81.57 g of toluene and 0.43 g of 36% hydrochloric acid. Further, keeping the temperature at 50° C., 18.98 g of 4,4'-methylenebis(2-hydroxymethyl-3,6-dimethylphenol) was added in portions thereto over 1 hour. The mixture was stirred at the same temperature for 3 hours. After cooling, the mixture was filtered and the obtained filtration mass was dissolved in 269 g of ethyl acetate. The solution was washed with 47.82 g of distilled water and the washing was repeated four times. The oil layer was concentrated and thereto 107.5 g of toluene was added to precipitate crystalline products. The crystalline products were filtered, washed with 44.54 g of toluene and the toluene washing was once repeated. The obtained wet cake was dried a whole day and night under reduced pressure at 45° C. to obtain 13.45 g of compound 1.

Mass spectrum: MS 497

$^1$H-NMR (dimethylsulfoxide) δ (ppm): 1.92 (s, 6H); 2.02 (s, 6H); 2.09 (s, 6H); 3.68 (s, 2H); 3.88 (s, 4H); 6.33(s, 2H); 6.48 (s, 2H); 6.70 (m, 4H); 7.94 (brs, 2H); 9.22 (brs, 2H).

(2) Production of quinonediazide sulfonic acid ester of compound 1

Into a 5 liter four-necked flask were charged 372.53 g of compound 1 obtained according to same method as (1), 403.02 g of 1,2-naphthoquinonediazide-5-sulfonyl chloride and 3877.73 g of 1,4-dioxane and they were completely dissolved. Then, 182.142 g of triethylamine was added dropwise at 20°–30° C. over 1 hour. After addition was completed, the mixture was stirred at 30° C. for 3 hours. Thereafter, 45.04 g of acetic acid was added and the mixture was stirred for 1 more hour. The reaction mixture was filtered and the residue was washed with 403.02 g of 1,4-dioxane. The combined filtrate and washing were poured into a mixture of 171 g of acetic acid and 17123 g of deionized water and stirred for 1 hour. The precipitated crystals were filtered and the filter cake was washed by stirring in 3891 g of deionized water. This washing operation was repeated further three times. The finally obtained filter cake was dried at 40° C. to obtain 747 g of the ester (hereinafter referred to as Photosensitizer A). $^1$H-NMR (dimethylsulfoxide) δ (ppm):

1.75 (S, 6H); 2.06 (S, 6H); 2.06 (S, 6H); 3.65 (s, 2H); 3.86 (s, 4H); 6.39 (S, 2H); 6.48 (s, 2H); 6.63 (d, 8.2 Hz, 2H); 6.89 (d, 8.2 Hz, 2H); 7.42 (d, 10 Hz, 2H); 7.66 (dd, 8.8 Hz, 2H); 7.75 (d, 10 Hz, 2H); 8.02 (s, 2H); 8.24 (d, 8 Hz, 2H); 8.60 (d, 8 Hz, 2H).

Synthesis Example 2

(1) Production of 2,2'-methylenebis(6-hydroxymethyl-4-methylphenol)

Into a 1 liter four-necked flask were charged 108.0 g of para-cresol, 20 g of sodium hydroxide and 200 g of water. While stirring at 60° C., 202.7 g of 37% formaldehyde was added dropwise thereto over 1 hour, and the reaction was conducted for 10 more hours. After completion of the reaction, 57.4 g of 36% hydrochloric acid was added and then 250 g of ethyl acetate was added thereto. The extracted mixture was washed with water and the oil layer was concentrated. To the concentrated product, 100 g of toluene was added, and the mixture was stirred for 2 hours at room temperature and then filtered, rinsed with toluene and dried to obtain 59.8g of 2,2'-methylenebis(6-hydroxymethyl-4-methylphenol).

Purity measured by liquid chromatography (LC): 98%

Mass spectrum: MS 288

$^1$H-NMR (dimethylsulfoxide) δ (ppm): 2.12 (s, 6H); 3.78 (s, 2H); 4.53 (s, 4H); 5.26 (brs, 2H); 6.70 (s, 2H); 6.86 (s, 2H); 8.41 (brs, 2H).

(2) Production of 2,2'-methylenebis[6-(2-hydroxy-5-methylbenzyl)-4-methylphenol](hereinafter referred to as compound 2)

Into a 200 ml four-necked flask were charged 0.48 g of para-toluene sulfonic acid, 54.07 g of para-cresol and 30.64 g of toluene. Further, keeping the temperature at 30° C., 7.21 g of 2,2'-methylenebis(6-hydroxymethyl-4-methylphenol) obtained above and having a purity of 98% was added in ten portions over 1 hour. The mixture was stirred at the same temperature for 3 hours. After completion of the reaction, 100 g of ethyl acetate was added. Thereafter, 50g of deionized water was added and the resulting mixture was stirred and a phase separation was carried out. Then, metal content was removed by adding 50 g of 1% aqueous oxalic acid solution, followed by stirring the mixture and by carrying out a phase separation. Thereafter, washing with 50 g of deionized water was repeated four times, and the oil phase was concentrated. To the concentrated mass, 100 g of toluene was added and the resulting solution was cooled to 20° C. and filtered. The filter cake was rinsed with 50 g of toluene and dried a whole day and night under reduced pressure at 45° C. to obtain 7.21 g of compound 2.

Purity (LC):97.1%

Mass spectrum: MS 468

(3) Production of quinonediazide sulfonic acid ester of compound 2

Into a 100 ml four-necked flask were charged 0.47 g of compound 2 obtained above, 0.54 g of 1,2-naphthoquinonediazide-5-sulfonyl chloride and 5.03 g of 1,4-dioxane and the temperature was adjusted to 25° C. Thereto, 0.24 g of triethylamine was added dropwise over 1 hour. After addition was completed, the mixture was stirred for 3 hours. Thereafter, 0.06 g of acetic acid was added for neutralization and the reaction mixture was filtered. The filtrate was added to a mixture of 0.3 g of acetic acid and 30 g of deionized water. The resulting mixture was stirred for 1 hour, filtered and washed. The finally obtained filter cake was dried a whole day and night at 45° C. under reduced pressure to obtain 0.92 g of the ester (hereinafter referred to as Photosensitizer B).

Mass spectrum of the main component: MS 932

Synthesis Example 3

(1) Production of 4-hydroxymethyl-2,5-dimethylphenol

Into a 5 liter four-necked flask were charged 610.9 g of 2,5-xylenol, 200 g of sodium hydroxide and 2500 g of water. While stirring at 12° C., 565 g of 37% formaldehyde was added dropwise thereto over 1 hour and 30 minutes, and the reaction was conducted for 4 more hours. After completion of the reaction, 89 g of 28% aqueous ammonia solution was added and the mixture was stirred for 30 minutes. Thereafter, 400 g of acetic acid was added thereto, and the resulting mixture was filtered and washed with water. The filtered product thus obtained was dried to obtain 609 g of 4-hydroxymethyl-2,5-dimethylphenol. Purity measured by liquid chromatography (LC): 99%

Mass spectrum: MS 152

$^1$H-NMR (dimethylsulfoxide) δ (ppm): 2.12 (s, 3H); 2.21 (s, 3H); 3.76 (brs, 1H); 4.50(s, 2H); 6.61 (s, 1H); 7.01 (s, 1H); 7.99 (brs, 1H).

(2) Production of 4-(4-hydroxy-3-methylbenzyl)-2,5-dimethylphenol

Into a 1 liter of four-necked flask were charged 4.76 g of para-toluenesulfonic acid, 54.07 g of ortho-cresol and 108.14 g of methanol. Further, keeping the temperature at 30° C., 38.05 g of 4-hydroxymethyl-2,5-dimethylphenol obtained above was added in ten portions over 1 hour. The mixture was stirred at the same temperature for 2 more hours. After completion of the reaction, 200 g of toluene and 200 g of ethyl acetate was added. Thereafter, 200 g of deionized water was added and the resulting mixture was stirred and a phase separation was carried out. Then, metal content was removed by adding 200 g of 1% aqueous oxalic acid solution, followed by stirring the mixture and by carrying out a phase separation. Thereafter, washing with 200 g of deionized water was repeated four times, and the oil phase was concentrated. To the concentrated mass, 200 g of toluene was added and the resulting solution was cooled to 20° C. and filtered. The filter cake was rinsed with 200 g of toluene and dissolved in 200 g of ethyl acetate. After adding 200 g of toluene thereto, the resulting mixture was concentrated. To the concentrated mass, 200 g of toluene was added and the resulting mass was cooled to 20° C. and filtered. The filter cake was rinsed with 200 g of toluene and dried a whole day and night under reduced pressure at 45° C. to obtain 20.12 g of 4-(4-hydroxy-3-methylbenzyl)-2,5-dimethylphenol.

Purity (LC): 90.05%

Mass spectrum: MS 242

$^1$H-NMR (dimethylsulfoxide) δ (ppm): 2.13 (s, 9H); 3.63 (s, 2H); 6.53 (s, 1H); 6.64 (d, J=7.9 Hz, 1H); 6.67 (d, J=7.9 Hz, 1H); 6.78 (s, 1H); 6.78 (s, 1H); 8.90 (s, 1H); 9.00 (s, 1H).

(3) Production of 2-hydroxymethyl-4-(4-hydroxy-3-hydroxymethyl-5-methylbenzyl)-3,6-dimethylphenol Into a 100 ml four-necked flask were charged 12.12 g of above-obtained 4-(4-hydroxy-3-methylbenzyl)-2,5-dimethylphenol having a purity of 90.05%, 4.8 g of sodium hydroxide and 48 g of water. While stirring at 40° C., 24.35 g of 37% formaldehyde was added dropwise thereto over 1 hour, and the reaction was conducted for 2 more hours. After completion of the reaction, 10 g of 90% aqueous acetic acid solution was added for neutralization and then the mixture was cooled to 25° C. The resulting mixture was filtered and rinsed with 100 g of deionized water. The filtered product was dissolved in 200 g of ethyl acetate, 50 g of toluene was added thereto and the resulting mixture was concentrated. To the concentrated mass, 200 g of toluene was added, and the mixture was cooled to 20° C., and then filtered. The filter cake was rinsed with 200 g of toluene and dried a whole day and night under reduced pressure at 45° C. to obtain 9.20 g of 2-hydroxymethyl-4-(4-hydroxy-3-hydroxymethyl-5-methylbenzyl)-3,6-dimethylphenol.

Purity measured by liquid chromatography (LC): 86%

Mass spectrum: MS 302

$^1$H-NMR (dimethylsulfoxide) δ (ppm): 2.05 (s, 3H); 2.07 (s, 3H); 2.08 (s, 3H); 3.70 (s, 2H); 4.47 (s, 2H); 4.62 (s, 2H); 5.70 (brs, 2H); 6.70 (s, 1H); 6.80 (S, 2H); 8.30 (brs, 2H).

(4) Production of 2-(2-hydroxy-5-methylbenzyl)-4-[4-hydroxy-3-(2-hydroxy-5-methylbenzyl)-5-methylbenzyl]-3,6-dimethylphenol(hereinafter referred to as compound 3)

Into a 100 ml of four-necked flask were charged 0.76 g of para-toluene sulfonic acid, 17.3 g of para-cresol and 17.3 g of toluene. Further, keeping the temperature at 30° C., 6.05 g of above-obtained 2-hydroxymethyl-4-(4-hydroxy-3-hydroxymethyl-5-methylbenzyl)-3,6-dimethylphenol having a purity of 86% was added in ten portions over 1 hour. The mixture was stirred at the same temperature for 2 more hours. After completion of the reaction, the mixture was filtered and rinsed with 200 g of toluene. The filtered product was dissolved in a mixed solvent consisting of 200 g of toluene and 200 g of ethyl acetate. Thereafter, 200 g of deionized water was added and the resulting mixture was stirred and a phase separation was carried out. Then, metal content was removed by adding 200 g of 1% aqueous oxalic acid solution, followed by stirring the mixture and by carrying out a phase separation. Thereafter, washing with 200 g of water was repeated four times, and the oil phase was concentrated. To the concentrated mass, 200 g of toluene was added and the resulting solution was cooled to 20° C. and filtered. The filter cake was rinsed with 200 g of toluene and dried a whole day and night under reduced pressure at 45° C. to obtain 3.52 g of compound 3.

Purity (LC): 95.8%

Mass spectrum: MS 482

$^1$H-NMR (dimethylsulfoxide) δ (ppm): 1.88 (s, 3H); 1.98 (s, 3H); 2.07 (s, 6H); 2.12 (s, 3H); 3.62 (s, 2H); 3.70 (s, 2H); 3.84 (s, 2H); 6.30 (s, 1H); 6.57 (s, 1H); 6.65 (d, J=7.9 Hz, 1H); 6.66 (s, 1H); 6.67 (s, 1H); 6.68 (s, 1H); 6.70 (d, J=7.9 Hz, 1H); 6.75 (d, J=7.9 Hz, 1H); 6.80 (d, J=7.9 Hz, 1H); 8.00 (brs, 2H); 9.31 (brs, 2H).

(5) Production of quinonediazide sulfonic acid ester of compound 3

Into a 100 ml four-necked flask were charged 0.96 g of compound 3 obtained above, 1.07 g of 1,2-naphthoquinonediazide-5-sulfonyl chloride and 10.2 g of 1,4-dioxane and the temperature was adjusted to 25° C. Thereto, 0.49 g of triethylamine was added dropwise over 1 hour. After addition was completed, the mixture was stirred for 3 hours. Thereafter, 0.13 g of acetic acid was added for neutralization and the reaction mixture was filtered. The filtrate was added to a mixture of 0. 5 g of acetic acid and 50 g of deionized water. The resulting mixture was stirred for 1 hour, filtered and washed. The finally obtained filter cake was dried a whole day and night at 45° C. under reduced pressure to obtain 1.88 g of the ester (hereinafter referred to as Photosensitizer C).

Mass spectrum of the main component: MS 946

$^1$H-NMR (dimethylsulfoxide) δ (ppm): 1.68 (s, 3H); 1.97 (s, 3H); 2.03 (s, 6H); 2.08 (s, 3H); 3.72 (s, 2H); 3.82 (s, 2H); 3.83 (s, 2H); 6.27 (s, 1H); 6.35 (s, 1H); 6.58 (s, 1H); 6.61 (d, J=7.9 Hz, 1H); 6.66 (d, J=7.9 Hz, 1H); 6.71 (s, 1H); 6.75 (s, 1H); 6.85 (d, J=7.9 Hz, 1H); 6.91 (d, J=7.9 Hz, 1H); 7.31 (d, J=8.3 Hz, 1H); 7.41 (d, J=8.3 Hz, 1H); 7.61 (d, J=8.2, 8.3 Hz, 1H); 7.62 (dd, J=8.2, 8.3 Hz, 1H); 7.73 (d, J=8.3 Hz, 1H); 7.74 (d, J=8.3 Hz, 1H); 8.05 (s, 1H); 8.08 (s, 1H); 8.16 (d, J=8.2 Hz, 1H); 8.24 (d, J=8.s Hz, 1H); 8.54 (d, J=8.3 Hz, 1H); 8.62 (d, J=8.3 Hz, 1H).

Synthesis Example 4

(1) Production of 4-(2-hydroxy-4.5-dimethylbenzyl)-2,5-dimethylphenol

Into a 1 liter of four-necked flask were charged 1.90 g of para-toluene sulfonic acid, 24.43 g of 3,4-xylenol and 48.87 g of toluene. Further, keeping the temperature at 30° C., 7.61 g of 4-hydroxymethyl-2,5-dimethylphenol was added in ten portions over 1 hour. The mixture was stirred at the same temperature for 2 more hours. After completion of the reaction, 50 g of toluene and 50 g of ethyl acetate was added. Thereafter, 50 g of deionized water was added and the resulting mixture was stirred and a phase separation was carried out. Then, metal content was removed by adding 50 g of 1% aqueous oxalic acid solution, followed by stirring the mixture and by carrying out a phase separation. Thereafter, washing with 50 g of deionized water was repeated four times, and the oil phase was concentrated. To the concentrated mass, 100 g of toluene was added and the resulting solution was cooled to 20° C. and filtered. The filter cake was rinsed with 200 g of toluene and dissolved in 50 g of ethyl acetate. After adding 200 g of toluene thereto, the resulting mixture was concentrated. To the concentrated mass, 100 g of toluene was added and the resulting mass was cooled to 20° C. and filtered. The filter cake was rinsed with 100 g of toluene and dried a whole day and night under reduced pressure at 45 ° C. to obtain 8.82 g of 4-(2-hydroxy-4,5-dimethylbenzyl)-2,5-dimethylphenol.

Purity (LC): 90.85%

Mass spectrum: MS 256

$^1$H-NMR (dimethylsulfoxide) δ (ppm): 1.99 (s, 3H); 2.01 (s, 3H); 2.06 (s, 3H); 2.09 (s, 3H); 3.60 (s, 2H); 6.46 (s, 1H); 6.56 (s, 1H); 6.59 (s, 1H); 6.70 (s, 1H); 8.88 (s, 1H); 8.94 (s, 1H).

(2) Production of 2-hydroxymethyl-4-(2-hydroxy-3-hydroxymethyl-4,5-dimethylbenzyl)-3,6-dimethylphenol Into a 100 ml four-necked flask were charged 7.69 g of the above-obtained 4-(2-hydroxy-4,5-dimethylbenzyl)-2,5-dimethylphenol having purity of 90.85%, 2.88 g of sodium hydroxide and 28.8 g of water and they were dissolved. While keeping the temperature at 40° C., 14.61 g of 37% formaldehyde was added dropwise thereto over one hour, and the mixture was stirred for one more hour. After completion of the reaction, 6 g of 90% aqueous acetic acid solution was added for neutralization and the mixture was cooled to 25 ° C. Thereafter, 100 g of ethyl acetate and 20 g of toluene were added thereto, followed by a phase separation. The solution thus obtained was concentrated to obtain 9.20 g of 2-hydroxymethyl-4-(2-hydroxy-3-hydroxymethyl-4,5-dimethylbenzyl)-3,6-dimethylphenol Purity measured by liquid chromatography (LC): 60%

Mass spectrum: MS 316

(3) Production of 2-(2-hydroxy-5-methylbenzyl)-4-[2-hydroxy-3-(2-hydroxy-5-methylbenzyl)-4,5-methylbenzyl]-3,6-dimethylphenol(hereinafter referred to as compound 4)

Into a 100 ml of four-necked flask were charged 0.95 g of para-toluene sulfonic acid, 21.63 g of para-cresol and 21.63 g of toluene. Further, keeping the temperature at 30° C., 7.91 g of 2-hydroxymethyl-4-(2-hydroxy-3-hydroxymethyl-4,5-dimethylbenzyl)-3,6-dimethylphenol obtained above and having a purity of 60% was added in ten portions over 1 hour. The mixture was stirred at the same temperature for one more hour. After completion of the reaction, the mixture was filtered and rinsed with 100 g of toluene. The filte cake was added to a mixed solvent of 50 g of toluene and 300 g of ethyl acetate. Thereafter, 200 g of deionized water was added thereto and the resulting mixture was stirred and a phase separation was carried out. Then, metal content was removed by adding 50 g of 1% aqueous oxalic acid solution, followed by stirring the mixture and by carrying out a phase separation. Thereafter, washing with 200 g of deionized water was repeated four times, and the oil phase was concentrated. To the concentrated mass, 200 g of toluene was added and the resulting solution was cooled to 20° C. and filtered. The filter cake was rinsed with 200 g of toluene and dried a whole day and night under reduced pressure at 45° C. to obtain 2.62 g of compound 4.

Purity (LC): 93.9%

Mass spectrum: MS 482

$^1$H-NMR (dimethylsulfoxide) δ (ppm): 1.88 (s, 3H); 1.93 (s, 3H); 1.96 (s, 6H); 2.00 (s, 3H); 2.13 (s, 3H); 3.75 (s, 2H); 3.88 (s, 4H); 6.32 (s, 1H); 6.35 (s, 1H); 6.38 (s, 1H); 6.66 (d, J=5.8 Hz, 1H); 6.70 (s, 1H); 6.71 (d, J=5.8 Hz, 1H); 6.74 (d, J=5.8 Hz, 1H); 6.75 (d, J=5.8 Hz, 1H); 7.97 (brs, 3H); 8.02 (brs, 1H); 9.21 (brs, 1H); 9.23 (brs, 1H).

(4) Production of quinonediazide sulfonic acid ester of compound 4

Into a 100 ml four-necked flask were charged 0.40 g of compound 4 obtained above, 0.43 g of 1,2-naphthoquinonediazide-5-sulfonyl chloride and 4.14 g of 1,4-dioxane and the temperature was adjusted to 25° C. Thereto, 0.19 g of triethylamine was added dropwise over 1 hour. After addition was completed, the mixture was stirred for 3 hours. Thereafter, 0.05 g of acetic acid was added for neutralization and the reaction mixture was filtered. The filtrate was added to a mixture of 0.4 g of acetic acid and 40 g of deionized water. The resulting mixture was stirred for 1 hour, filtered and washed. The finally obtained filter cake was dried a whole day and night at 45° C. under reduced pressure to obtain 0.74 g of the ester (hereinafter referred to as Photosensitizer D).

Mass spectrum of the main component: MS 960

$^1$H-NMR (dimethylsulfoxide) δ (ppm): 1.70 (s, 3H); 1.78 (s, 3H); 1.99 (s, 3H); 2.04 (s, 3H); 2.07 (s, 3H); 2.13 (s, 3H); 3.74 (s, 2H); 3.85 (brs; 4H); 6.34 (s, 1H); 6.40 (brs, 2H); 6.63 (d, J=7.1 Hz, 1H); 6.66 (d, J=7.1 Hz, 1H); 6.70 (s, 1H); 6.89 (s, 1H); 6.94 (s, 1H); 7.43 (d, J=6.8 Hz, 1H); 7.47 (d, J=6.8 Hz, 1H); 7.64 (m, 1H); 7.67 (m, 1H); 7.74 (d, J=6.8 Hz, 1H); 7.79 (d, J=6.8 Hz, 1H); 8.08 (brs, 1H); 8.12 (brs, 1H); 8.23 (d, J=7.2 Hz, 1H); 8.27 (d, J=7.2 Hz, 1H); 8.60 (d, J=7.3 Hz, 1H); 8.64 (d, J=7.3 Hz, 1H).

Synthesis Example 5

(1) Production of 4,4'-methylenebis[2-(2-hydroxy-5-methylbenzyl)-6-methylphenol](hereinafter referred to as compound 5)

Into a 500 ml three-necked flask were charged 54.07 g of para-cresol, 30.64 g of toluene and 0.48 g of para-toluene sulfonic acid. Further, keeping the temperature at 50° C., 7.21 g of 4,4'-methylenebis(2-hydroxymethyl-6-methylphenol) was added in portions thereto over 1 hour. The mixture was stirred at the same temperature for 3 hours. After completion of the reaction, 200 g of ethyl acetate was added thereto and the resulting mixture was washed with 50 g of distilled water. The washing was repeated four more times. The oil layer was concentrated and thereto 50 g of toluene was added to precipitate crystalline products. The crystalline products were filtered out and rinsed with 50 g of toluene two times. The obtained wet cake was dried a whole day and night under reduced pressure at 45° C. to obtain 3.26 g of compound 5.

Mass spectrum: MS 468

$^1$H-NMR (dimethylsulfoxide) δ (ppm): 2.08 (s, 6H); 2.10 (s, 6H); 3.52 (s, 2H); 3.72 (s, 4H); 6.63 (s, 2H); 6.74 (m, 6H); 6.80 (m, 2H); 8.10 (s, 2H); 9.41 (brs, 2H).

(2) Production of quinonediazide sulfonic acid ester of compound 5

Into a 100 ml four-necked flask were charged 0.42 g of compound 5 obtained above, 0.48 g of 1,2-naphthoquinonediazide-5-sulfonyl chloride and 4.53 g of 1,4-dioxane and they were completely dissolved. Then, 0.22 g of triethylamine was added dropwise at 20°–30° C. over 1 hour. After addition was completed, the mixture was stirred at 30° C. for 3 hours. Thereafter, 0.05 g of acetic acid was added for neutralization and the mixture was filtered. The filtrate was poured into a mixture of 0.4 g of acetic acid and 40 g of deionized water and stirred for 1 hour. Then the mixture was filtered and washed. The finally obtained filter cake was dried at 40° C. to obtain 0.82 g of the ester (hereinafter referred to as Photosensitizer E).

Mass spectrum of the main component: MS 932

Synthesis Example 6

(1) Production of 1,1-bis(4-hydroxy-3-hydroxymethyl-5-methylphenyl)-1-phenylethane Into a 100 ml four-necked flask were charged 25.47 g of 1,1-bis(4-hydroxy-3-methylphenyl)-1-phenylethane["Bis-OC-AP" manufactured by Honshu Kagaku Co., Ltd.], 4.48 g of sodium hydroxide and 44.8 g of water. While stirring at 50° C., 25.97 g of 37% formaldehyde was added dropwise thereto over 1 hour, and the reaction was conducted for 1 more hour. After completion of the reaction, 11 g of 90% aqueous acetic acid solution was added for neutralization and then the mixture was cooled to 25° C. Thereafter, 100 g of ethyl acetate and 20 g of toluene were added thereto and a phase separation was carried out. Then, the resulting mixture was concentrated to obtain 30.2 g of 1,1-bis(4-hydroxy-3-hydroxymethyl-5-methylphenyl)-1-phenylethane. Purity measured by liquid chromatography (LC): 85%

Mass spectrum: MS 378

$^1$H-NMR (dimethylsulfoxide) δ (ppm): 1.90 (s, 3H); 2.07 (s, 6H); 4.50 (s, 4H); 6.65 (brs, 1H); 6.70 (brs, 1H); 6.82 (brs, 2H); 7.03 (s, 1H); 7.06 (s, 1H); 7.16 (m, 1H); 7.25 (m, 2H); 6.50–8.50 (4H).

(2) Production of 1,1-bis[4-hydroxy-3-(2-hydroxy-5-methylbenzyl)-5-methylphenyl]-1-phenylethane (hereinafter referred to as compound 6)

Into a 100 ml four-necked flask were charged 0.38 g of para-toluene sulfonic acid, 3.24 g of para-cresol and 6.49 g of toluene. Further, keeping the temperature at 30° C., 3.78 g of 1,1-bis(4-hydroxy-3-hydroxymethyl-5-methylphenyl)-1-phenylethane obtained above and having a purity of 85% was added in ten portions over 1 hour. The mixture was stirred at the same temperature for one hour. After completion of the reaction, 30 g of ethyl acetate was added. Thereafter, 50 g of deionized water was added and the resulting mixture was stirred and a phase separation was carried out. Then, metal content was removed by adding 5 g of 1% aqueous oxalic acid solution, followed by stirring the mixture and by carrying out a phase separation. Thereafter, washing with 50 g of deionized water was repeated four times, and the oil phase was concentrated. The concentrated mass was subjected to a separation with a silica-gel column chromatography to obtain 1.5 g of compound 6.

Purity (LC): 95.6%

Mass spectrum: MS 522

$^1$H-NMR (dimethylsulfoxide) δ (ppm): 1.92 (s, 3H); 2.04 (s, 6H); 2.06 (s, 6H); 3.68 (s, 4H); 6.55 (brs, 2H); 6.59 (brs, 2H); 6.65 (m, 4H); 6.75 (m, 2H); 7.00 (d, J=8.8 Hz, 2H); 7.14 (m, 1H); 7.20 (m, 2H); 8.10 (s, 2H); 9.34 (s, 2H).

(3) Production of quinonediazide sulfonic acid ester of compound 6

Into a 100 ml four-necked flask were charged 0.84 g of compound 6 obtained above, 0.81 g of 1,2-naphthoquinonediazide-5-sulfonyl chloride and 8.22 g of 1,4-dioxane and the temperature was adjusted to 25° C. Thereto, 0.36 g of triethylamine was added dropwise over 1 hour. After addition was completed, the mixture was stirred for 3 hours. Thereafter, 0.09 g of acetic acid was added for neutralization and the reaction mixture was filtered. The filtrate was added to a mixture of 0.5 g of acetic acid and 50 g of deionized water. The resulting mixture was stirred for 1 hour, filtered and washed. The finally obtained filter cake was dried a whole day and night at 45° C. under reduced pressure to obtain 1.57 g of the ester (hereinafter referred to as Photosensitizer F).

Mass spectrum of the main component: MS 1022

Synthesis Example 7

(1) Production of 1,1-bis(4-hydroxy-3-hydroxymethyl-5-methylphenyl)-cyclohexane

Into a 100 ml four-necked flask were charged 23.71 g of 1,1-bis(4-hydroxy-3-methylphenyl)-cyclohexane["Bis-OC—Z" manufactured by Honshu Kagaku Co., Ltd.], 4.48 g of sodium hydroxide and 44.8 g of water. While stirring at 50° C., 25.97 g of 37% formaldehyde was added dropwise thereto over 1 hour, and the reaction was conducted for 1 more hour. After completion of the reaction, 11 g of 90% aqueous acetic acid solution was added for neutralization and then the mixture was cooled to 25° C. Thereafter, 100 g of ethyl acetate and 20 g of toluene were added thereto and a phase separation was carried out. Then, the resulting mixture was concentrated to obtain 28.5 g of 1,1-bis(4-hydroxy-3-hydroxymethyl-5-methylphenyl)-cyclohexane.

Purity measured by liquid chromatography (LC): 79%

Mass spectrum: MS 356

$^1$H-NMR (dimethylsulfoxide) δ (ppm): 1.44 (brs, 6H); 2.08 (s, 6H); 2.14 (brs, 4H); 4.50 (d, J=6.3 Hz, 4H); 5.25 (t, J=6.3 Hz, 2H); 6.85 (s, 2H); 7.00 (s, 1H); 8.16 (brs, 2H).

(2) Production of 1,1-bis[4-hydroxy-3-(2-hydroxy-5-methylbenzyl)-5-methylphenyl]-cyclohexane (hereinafter referred to as compound 7)

Into a 100 ml four-necked flask were charged 0.38 g of para-toluene sulfonic acid, 8.65 g of para-cresol and 17.30 g of toluene. Further, keeping the temperature at 30° C., 3.78 g of 1,1-bis(4-hydroxy-3-hydroxymethyl-5-methylphenyl)-1-cyclohexane obtained above and having a purity of 79% was added in ten portions over 1 hour. The mixture was stirred at the same temperature for one hour. After completion of the reaction, 30 g of ethyl acetate was added. Thereafter, 50 g of deionized water was added and the resulting mixture was stirred and a phase separation was carried out. Then, metal content was removed by adding 50 g of 1% aqueous oxalic acid solution, followed by stirring the mixture and by carrying out a phase separation. Thereafter, washing with 50 g of deionized water was repeated four times, and the oil phase was concentrated. The concentrated mass was subjected to a separation with a silica-gel column chromatography to obtain 0.7 g of compound 7.

Purity (LC): 95.6%

Mass spectrum: MS 536

$^1$H-NMR (dimethylsulfoxide) δ (ppm): 1.38 (brs, 6H); 2.05 (brs, 4H); 2.07 (s, 6H); 2.08 (s, 6H); 3.71 (s, 4H); 6.67 (d, J=6.8 Hz, 2H); 6.70 (s, 2H); 6.71 (s, 2H); 6.79 (d, J=6.8 Hz, 2H); 6.90 (s, 2H); 8.00 (s, 2H); 9.29 (s, 2H).

(3) Production of quinonediazide sulfonic acid ester of compound 7

Into a 100 ml four-necked flask were charged 0.70 g of compound 7 obtained above, 0.70 g of 1,2- naphthoquinonediazide-5-sulfonyl chloride and 6.98 g of 1,4-dioxane and the temperature was adjusted to 25° C. Thereto, 0.32 g of triethylamine was added dropwise over 1 hour. After addition was completed, the mixture was stirred for 3 hours. Thereafter, 0.08 g of acetic acid was added for neutralization and the reaction mixture was filtered. The filtrate was added to a mixture of 0.5 g of acetic acid and 50 g of deionized water. The resulting mixture was stirred for 1 hour, filtered and washed. The finally obtained filter cake was dried a whole day and night at 45° C. under reduced pressure to obtain 1.34 g of the ester (hereinafter referred to as Photosensitizer G).

Mass spectrum of the main component: MS 1000

Synthesis Example 8

(1) Production of 2,2-bis(4-hydroxy-3-hydroxymethyl-5-isopropylphenyl)-propane

Into a 100 ml four-necked flask were charged 25.00 g of 2,2-bis(4-hydroxy-3-isopropylphenyl)propane["Bis-OIPP-A" manufactured by Honshu Kagaku Co., Ltd.], 4.48 g of sodium hydroxide and 44.8 g of water. While stirring at 50° C., 25.97 g of 37% formaldehyde was added dropwise thereto over 1 hour, and the reaction was conducted for 1 more hour. After completion of the reaction, 11 g of 90% aqueous acetic acid solution was added for neutralization and then the mixture was cooled to 25° C. Thereafter, 100 g of ethyl acetate and 20 g of toluene were added thereto and a phase separation was carried out. Then, the resulting mixture was concentrated to obtain 28.2 g of 2,2-bis(4-hydroxy-3-hydroxymethyl-5-isopropylphenyl)propane.

Purity measured by liquid chromatography (LC): 82%
Mass spectrum: MS 372
$^1$H-NMR (dimethylsulfoxide) δ (ppm): 1.06 (s, 6H); 1.08 (s, 6H); 1.55 (s, 6H); 3.20 (m, 2H); 4.52 (s, 4H); 5.40 (brs, 2H); 6.82 (s, 2H); 6.90 (s, 2H); 8.20 (brs, 2H).

(2) Production of 2,2-bis[4-hydroxy-3-(2-hydroxy-5-methylbenzyl) -5-isopropylphenyl ]-propane (hereinafter referred to as compound 8)

Into a 100 ml four-necked flask were charged 0.38 g of para-toluene sulfonic acid, 8.65 g of para-cresol and 17.30 g of toluene. Further, keeping the temperature at 30° C., 3.73 g of 2,2-bis(4-hydroxy-3-hydroxymethyl-5-isopropylphenyl)propane obtained above and having a purity of 82% was added in ten portions over 1 hour. The mixture was stirred at the same temperature for one hour. After completion of the reaction, 30 g of ethyl acetate was added. Thereafter, 50 g of deionized water was added and the resulting mixture was stirred and a phase separation was carried out. Then, metal content was removed by adding 50 g of 1% aqueous oxalic acid solution, followed by stirring the mixture and by carrying out a phase separation. Thereafter, washing with 50 g of deionized water was repeated four times, and the oil phase was concentrated. The concentrated mass was subjected to a separation with a silica-gel column chromatography to obtain 0.3 g of compound 8.

Purity (LC): 96.6%
Mass spectrum: MS 552

(3) Production of quinonediazide sulfonic acid ester of compound 8

Into a 100 ml four-necked flask were charged 0.33 g of compound 8 obtained above, 0.32 g of 1,2-naphthoquinonediazide-5-sulfonyl chloride and 3.27 g of 1,4-dioxane and the temperature was adjusted to 25° C. Thereto, 0.15 g of triethylamine was added dropwise over 1 hour. After addition was completed, the mixture was stirred for 3 hours. Thereafter, 0.04 g of acetic acid was added for neutralization and the reaction mixture was filtered. The filtrate was added to a mixture of 0.3 g of acetic acid and 30 g of deionized water. The resulting mixture was stirred for 1 hour, filtered and washed. The finally obtained filter cake was dried a whole day and night at 45° C. under reduced pressure to obtain 0.64 g of the ester (hereinafter referred to as Photosensitizer H).

Mass spectrum of the main component: MS 1016

Example 1

(1) Production of 2,6-bis(4-hydroxy-3-hydroxymethyl-2,5-dimethylbenzyl)-4-methylphenol Into a 3 liter four-necked flask were charged 263.6 g of 2,6-bis(4-hydroxy-2,5-dimethylbenzyl)-4-methylphenol, 67.2 g of sodium hydroxide, 1169.3 g of water and 107.5 g of tetrahydrofuran and they were completely dissolved. While stirring at 40° C., 340.9 g of 37% formaldehyde was added dropwise thereto over 1 hour, and the reaction was conducted for 2 more hours. After completion of the reaction, 134.4 g of 90% aqueous acetic acid solution was added for neutralization and then the mixture was cooled to 25° C. Thereafter, the precipitated crystalline product was filtered out and rinsed with 1000 g of deionized water. The resulting product was dried a whole day and night under reduced pressure at 45° C. to obtain 265 g of 2,6-bis(4-hydroxy-3-hydroxymethyl-2,5-dimethylbenzyl)-4-methylphenol Purity measured by liquid chromatography (LC): 80%
Mass spectrum: MS 436
$^1$H-NMR (dimethylsulfoxide) δ (ppm): 1.95 (s, 3H); 2.05 (s, 6H); 2.10 (s, 6H); 3.78 (S, 4H); 4.65 (s, 4H); 5.23 (brs, 2H); 6.31 (s, 2H); 6.70 (s, 2H); 8.18 (brs, 1H); 8.60 (brs, 2H).

(2) Production of 2,6-bis[4-hydroxy-3-(2-hydroxy-5-methylbenzyl)-2,5-dimethylbenzyl]-4-methylphenol (hereinafter referred to as compound 9)

Into a 1 liter of four-necked flask were charged 1.90 g of para-toluenesulfonic acid, 86.51 g of para-cresol and 176.83 g of toluene. Further, keeping the temperature at 30° C., 21.83 g of 2,6-bis(4-hydroxy-3-hydroxymethyl-2,5-dimethylbenzyl)-4-methylphenol obtained above and having a purity of 80% was added in ten portions over 1 and half hours. The mixture was stirred at the same temperature for three more hours. After completion of the reaction, the mixture was filtered and rinsed with 200 g of toluene. The filter cake was added to a mixed solvent of 200 g of toluene and 400 g of ethyl acetate and dissolved at 60° C. Thereafter, 400 g of deionized water was added thereto and the resulting mixture was stirred and a phase separation was carried out. Then, metal content was removed by adding 400 g of 1% aqueous oxalic acid solution, followed by stirring the mixture and by carrying out a phase separation. Thereafter, washing with 400 g of deionized water was repeated four times, and the oil phase was concentrated. To the concentrated mass, 200 g of toluene was added and the resulting solution was cooled to 20° C. and filtered. The filter cake was rinsed with 200 g of toluene and dried a whole day and night under reduced pressure at 45° C. to obtain 22.87 g of compound 9.

Purity (LC): 94.6%
Mass spectrum: MS 616
$^1$H-NMR (dimethylsulfoxide) δ (ppm): 1.88 (s, 6H); 1.95 (s, 3H); 2.03 (s, 6H); 2.13 (s, 6H); 3.78 (s, 4H); 3.88 (s, 4H); 6.28 (s, 2H); 6.32 (s, 2H); 6.68 (d, J=8.2 Hz, 2H); 6.70 (s, 2H); 6.74 (d, J=8.2 Hz, 2H); 7.95 (brs, 2H); 8.12 (brs, 1H); 9.20 (brs, 2H).

(3) Production of quinonediazide sulfonic acid ester of compound 9

Into a 100 ml four-necked flask were charged 1.85 g of compound 9 obtained above, 1.61 g of 1,2- naphthoquinonediazide-5-sulfonyl chloride and 17.33 g of 1,4-dioxane and the temperature was adjusted to 25° C. Thereto, 0.73 g of triethylamine was added dropwise over 1 hour. After addition was completed, the mixture was stirred for 3 hours Thereafter, 0.18 g of acetic acid was added for neutralization and the reaction mixture was filtered. The filtrate was added to a mixture of 0.8 g of acetic acid and 80 g of deionized water. The resulting mixture was stirred for 1 hour, filtered and washed. The finally obtained filter cake was dried a whole day and night at 45° C. under reduced pressure to obtain 3.23 g of the ester (hereinafter referred to as Photosensitizer I).

Mass spectrum of the main component: MS 1080

$^1$H-NMR (dimethylsulfoxide) δ (ppm): 1.70 (s, 6H); 1.95 (s, 3H); 2.05 (s, 6H); 2.13 (s, 6H); 3.75 (s, 4H); 3.86 (s, 4H); 6.22 (s, 2H); 6.40 (s, 2H); 6.65 (d, J=8.2 Hz, 2H); 6.72 (s, 2H); 6.88 (d, J=8.2 Hz, 2H); 7.42 (d, J=7.9 Hz, 2H); 7.64 (t, J=7.9 Hz, 2H); 7.75 (d, J=7.9 Hz, 2H); 8.04(s, 2H); 8.15 (s, 1H); 8.25 (d, J=7.9 Hz, 2H); 8.62 (d, J=7.9 Hz, 2H).

Synthesis Example 9

(1) Production of 2,4-bis(hydroxymethyl)-3,5,6-trimethylphenol

Into a 2 liter four-necked flask were charged 136.19 g of 2,3,5-trimethylphenol, 48.0 g of sodium hydroxide and 480 g of water. While stirring at 40° C., 486.91 g of 37% formaldehyde was added dropwise thereto over one hour, and the reaction was conducted for 3 more hours. After completion of the reaction, 180.15 g of 90% aqueous acetic acid solution was added for neutralization, then the mixture was cooled to 25° C. and filtered. The filtrate was extracted with 1000 g of ethyl acetate and the ethyl acetate layer was washed with water and concentrated. To the concentrated mass, 500 g of toluene was added and the mixture was cooled to 20° C. and filtered. The filter cake thus obtained was rinsed with 400 g of toluene and dried a whole day and night at 45° C. under reduced pressure to obtain 100 g of 2,4-bis(hydroxymethyl)-3,5,6-trimethylphenol.

Purity measured by liquid chromatography (LC): 90%
Mass spectrum: MS 196

$^1$H-NMR (dimethylsulfoxide) δ (ppm): 2.06 (s, 3H); 2.19 (s, 3H); 2.21 (s, 3H); 4.41 (d, J=8.2 Hz, 2H); 4.43 (t, J=8.2 Hz, 1H); 4.62 (s, 2H); 5.41 (brs, 1H); 8.80 (brs, 1H).

(2) Production of 2,4-bis(4-hydroxy-2,5-dimethylbenzyl)-3,5,6-trimethylphenol

Into a 5 liter of four-necked flask were charged 5.88 g of sulfuric acid, 293.2 g of 2,5-xylenol and 293.2 g of methanol. Further, keeping the temperature at 30° C., 117.75 g of 2,4-bis(hydroxymethyl)-3,5,6-trimethylphenol obtained according to same method as (1) and having purity of 90% was added in ten portions over 1 hour. The mixture was stirred at the same temperature for 2 more hours. After completion of the reaction, 500 g of toluene and 1000 g of ethyl acetate was added. Thereafter, 1000 g of deionized water was added and the resulting mixture was stirred and a phase separation was carried out. Then, metal content was removed by adding 1000 g of 1% aqueous oxalic acid solution, followed by stirring the mixture and by carrying out a phase separation. Thereafter, washing with 1000 g of deionized water was repeated four times, and the oil phase was concentrated. To the concentrated mass, 500 g of toluene was added and the resulting solution was cooled to 20° C. and filtered. The filter cake was rinsed with 200 g of toluene and dissolved in 500 g of ethyl acetate and the oil phase was concentrated. To the concentrated mass, 500 g of toluene was added and the resulting mass was cooled to 20° C. and filtered. The filter cake was rinsed with 200 g of toluene and dried a whole day and night under reduced pressure at 45° C. to obtain 98.6 g of 2,4-bis(4-hydroxy-2,5-dimethylbenzyl)-3,5,6-trimethylphenol.

Purity (LC): 99.38%
Mass spectrum: MS 404

$^1$H-NMR (dimethylsulfoxide) δ (ppm): 1.81 (s, 3H); 1.89 (s, 6H); 2.00 (s, 3H); 2.12 (s, 3H); 2.22 (s, 6H); 3.68 (s, 2H); 3.78 (a, 2H); 6.08 (s, 1H); 6.15 (s, 1H); 6.58 (s, 1H); 6.60 (s, 1H); 7.80 (s, 1H); 8.80 (s, 1H); 8.85 (s, 1H).

(3) Production of 2,4-bis(4-hydroxy-3-hydroxymethyl-2,5-dimethylbenzyl)-3,5,6-trimethylphenol Into a 500 ml four-necked flask were charged 40.45 g of above-obtained 2,4-bis(4-hydroxy-2,5-dimethylbenzyl)-3,5,6-trimethylphenol having a purity of 99.38%, 14.4 g of sodium hydroxide, 144 g of water and 14.4 g of tetrahydrofuran and they were completely dissolved. While stirring at 40° C., 48.69 g of 37% formaldehyde was added dropwise thereto over 1 hour, and the reaction was conducted for 3 more hours. After completion of the reaction, 18.02 g of 90% aqueous acetic acid solution was added for neutralization and then the mixture was cooled to 25° C. The resulting mixture was filtered and the filtered product was dissolved in a mixed solvent consisting of 100 g of ethyl acetate and 14.40 g of tetrahydrofurane. The resulting solution was washed with water and the oil phase was concentrated. To the concentrated product, 100 g of toluene was added, and the mixture was cooled to 20° C., and then filtered. The filter cake was rinsed with 100 g of toluene and dried a whole day and night under reduced pressure at 45° C. to obtain 36.8 g of 2,4-bis(4-hydroxy-3-hydroxymethyl-2,5-dimethylbenzyl)-3,5,6-trimethylphenol.

Purity measured by liquid chromatography (LC): 75%
Mass spectrum: MS 464

$^1$H-NMR (dimethylsulfoxide) δ (ppm): 1.78 (s, 3H); 1.93 (s, 6H); 2.01 (s, 3H); 2.13 (s, 3H); 2.26 (s, 6H); 3.71 (s, 2H); 3.81 (s, 2H); 4.67 (s, 4H); 5.22 (brs, 2H); 6.08 (s, 1H); 6.13 (s, 1H); 7.78 (brs, 1H); 8.46 (brs, 1H); 8.47 (brs, 1H).

(4) Production of 2,4-bis[4-hydroxy-3-(2-hydroxy-5-methylbenzyl)-2,5-dimethylbenzyl]-3,5,6-trimethylphenol (hereinafter referred to as compound 10)

Into a 200 ml of four-necked flask were charged 0.57 g of para-toluene sulfonic acid, 38.93 g of para-cresol and 38.93 g of toluene. Further, keeping the temperature at 30° C., 13.94 g of above-obtained 2,4-bis(4-hydroxy-3-hydroxymethyl-2,5-dimethylbenzyl)-3,5,6-trimethylphenol having a purity of 75% was added in ten portions over 1 and half hour. The mixture was stirred at the same temperature for 2 more hours. After completion of the reaction, the precipitated crystalline product was filtered out and rinsed with 100 g of toluene. The filtered product was dissolved in a mixed solvent consisting of 100 g of toluene and 200 g of ethyl acetate at 60° C. Thereafter, 200 g of deionized water was added and the resulting mixture was stirred and a phase separation was carried out. Then, metal content was removed by adding 200 g of 1% aqueous oxalic acid solution, followed by stirring the mixture and by carrying out a phase separation. Thereafter, washing with 200 g of water was repeated four times, and the oil phase was concentrated. To the concentrated mass, 100 g of toluene was added and the resulting solution was cooled to 20° C. and filtered. The filter cake was rinsed with 100 g of toluene and dried a whole day and night under reduced pressure at 45° C. to obtain 10.3 g of compound 10.

Purity (LC): 94.9%
Mass spectrum: MS 644

$^1$H-NMR (dimethylsulfoxide) δ (ppm): 1.81 (s, 3H); 2.01 (s, 12H); 2.11 (s, 6H); 2.16 (s, 3H); 2.29 (s, 3H); 3.72 (s, 2H); 3.82 (s, 2H); 3.90 (s, 4H); 6.10 (s, 1H); 6.18 (s, 2H);

6.38 (s, 1H); 6.40 (s, 1H); 6.70 (d, J=7.1 Hz, 2H); 6.75 (d, J=7.1 Hz, 2H); 7.93 (brs, 3H); 9.24 (brs, 2H). (5) Production of quinonediazide sulfonic acid ester of compound 10

Into a 100 ml four-necked flask were charged 0.97 g of compound 10 obtained above, 0.81 g of 1,2-naphthoquinonediazide-5-sulfonyl chloride and 8.87 g of 1,4-dioxane and the temperature was adjusted to 25° C. Thereto, 0.36 g of triethylamine was added dropwise over 1 hour. After addition was completed, the mixture was stirred for 3 hours. Thereafter, 0.09 g of acetic acid was added for neutralization and the reaction mixture was filtered. The filtrate was added to a mixture of 0.5 g of acetic acid and 50 g of deionized water. The resulting mixture was stirred for 1 hour and the precipitated crystalline product was filtered and washed. The finally obtained filter cake was dried a whole day and night at 45° C. under reduced pressure to obtain 1.65 g of the ester (hereinafter referred to as Photosensitizer J).

Mass spectrum of the main component: MS 1108

$^1$H-NMR (dimethylsulfoxide) δ (ppm): 1.79 (s, 3H); 1.95 (s, 12H); 2.00 (s, 3H); 2.04 (s, 6H); 2.17 (s, 3H); 3.70 (s, 2H); 3.80 (s, 2H); 3.87 (s, 2H); 3.90 (s, 2H); 6.10 (s, 1H); 6.17 (s, 1H); 6.40 (s, 1H); 6.45 (s, 1H); 6.65 (d, J=7.8 Hz, 2H); 6.90 (d, J=7.8 Hz, 2H); 7.44 (d, J=7.4 Hz, 2H); 7.69 (t, J=7.2 Hz, 2H); 7.76 (d, J=7.4 Hz, 2H); 7.91 (brs, 3H); 8.26 (d, J=7.2 Hz, 2H); 8.61 (d, J=7.2 Hz, 2H).

Synthesis Example 10

(1) Production of 1,4-bis[1-(4-hydroxy-3-hydroxymethyl-5-methylphenyl)-1-methylethyl]benzene Into a 100 ml four-necked flask were charged 29.96 g of 1,4-bis[1-(4-hydroxy-3-methylphenyl)-1-methylethyl] benzene ["Bis-OC-P" manufactured by Honshu Kagaku Co., Ltd.], 4.48 g of sodium hydroxide and 44.8 g of water. While stirring at 50° C., 25.97 g of 37% formaldehyde was added dropwise thereto over 1 hour, and the reaction was conducted for 1 more hour. After completion of the reaction, 11 g of 90% aqueous acetic acid solution was added for neutralization and then the mixture was cooled to 25° C. Thereafter, 100 g of ethyl acetate and 20 g of toluene were added thereto and a phase separation was carried out. The separated solution was concentrated and 100 g of hexane was added to the concentrated mass and it was cooled to 25° C. The resulting mixture was filtered, and the filtered product was rinsed with 100 g of hexane and dried a whole day and night at 45° C. under reduced pressure to obtain 28.75 g of 1,4-bis[1-(4-hydroxy-3-hydroxymethyl-5-methylphenyl)-1-methylethyl]benzene Purity measured by liquid chromatography (LC): 90%
Mass spectrum: MS 434

$^1$H-NMR (dimethylsulfoxide) δ (ppm): 1.55 (s, 12H); 2.10 (s, 6H); 4.50 (s, 4H); 5.25 (brs, 2H); 6.80 (s, 2H); 6.93 (s, 2H); 7.07 (s, 4H); 8.22 (brs, 2H).

(2) Production of 1,4-bis[1-{4-hydroxy-3-(2-hydroxy-5-methylbenzyl)-5-methylphenyl}-1-methylethyl]benzene (hereinafter referred to as compound 11)

Into a 100 ml four-necked flask were charged 0.76 g of para-toluene sulfonic acid, 17.3 g of para-cresol and 34.6 g of toluene. Further, keeping the temperature at 30° C., 8.69 g of 1,4-bis[1-(4-hydroxy-3-hydroxymethyl-5-methylphenyl)-1-methylethyl]benzene obtained above and having a purity of 90% was added in ten portions over 1 hour. The mixture was stirred at the same temperature for one hour. After completion of the reaction, 30 g of ethyl acetate was added. Thereafter, 50 g of deionized water was added and the resulting mixture was stirred and a phase separation was carried out. Then, metal content was removed by adding 50 g of 1% aqueous oxalic acid solution, followed by stirring the mixture and by carrying out a phase separation. Thereafter, washing with 50 g of deionized water was repeated four times, and the oil phase was concentrated. To the concentrated mass, 100 g of toluene was added, and the resulting mixture was cooled to 25° C. and filtered. The filtered product was rinsed with 100 g of toluene and dried a whole day and night at 45° C. under reduced pressure to obtain 6.82 g of compound 11.

Purity (LC): 95%
Mass spectrum: MS 614

$^1$H-NMR (dimethylsulfoxide) δ (ppm): 1.51 (s, 12H); 2.05 (s, 6H); 2.10 (s, 6H); 3.72 (s, 4H); 6.65 (d, J=6.9 Hz, 2H); 6.70 (s, 2H); 6.75 (s, 2H); 6.79 (d, J=6.9 Hz, 2H); 6.84 (s, 2H); 7.02 (s, 4H); 8.10 (s, 2H); 9.38 (s, 2H).

(3) Production of quinonediazide sulfonic acid ester of compound 11

Into a 100 ml four-necked flask were charged 0.61 g of compound 11 obtained above, 0.54 g of 1,2-naphthoquinonediazide-5-sulfonyl chloride and 5.76 g of 1,4-dioxane and the temperature was adjusted to 25° C. Thereto, 0.24 g of triethylamine was added dropwise over 1 hour. After addition was completed, the mixture was stirred for 3 hours. Thereafter, 0.06 g of acetic acid was added for neutralization and the reaction mixture was filtered. The filtrate was added to a mixture of 0.5 g of acetic acid and 50 g of deionized water. The resulting mixture was stirred for 1 hour, filtered and washed. The finally obtained filter cake was dried a whole day and night at 45° C. under reduced pressure to obtain 1.11 g of the ester (hereinafter referred to as Photosensitizer K).

Mass spectrum of the main component: MS 1078

Synthesis Example 11

(1) Production of 2,6-dihydroxymethyl-3,4-dimethylphenol

Into a 2 liter four-necked flask were charged 122.17 g of 3,4-xylenol, 48.0 g of sodium hydroxide and 480 g of water. While stirring at 40° C., 486.9 g of 37% formaldehyde was added dropwise thereto over one hour, and the reaction was conducted for one more hour. After completion of the reaction, 180.2 g of acetic acid was added. The precipitated crystalline product was filtered out, rinsed with deionized water and dried a whole day and night at 45° C. under reduced pressure to obtain 139.8 g of 2,6-dihydroxymethyl-3,4-dimethylphenol.

Purity measured by liquid chromatography (LC): 95.4%
Mass spectrum: MS 182

$^1$H-NMR (dimethylsulfoxide) δ (ppm): 2.18 (s, 6H); 4.68 (s, 2H); 4.84 (s, 2H); 3.80 (brs, 2H); 6.89 (s, 1H); 9.12 (brs, 1H).

(2) Production of 2,6-bis(4-hydroxy-2,5-dimethylbenzyl)-3,4-dimethylphenol

Into a 1 liter of four-necked flask were charged 4.90 g of sulfuric acid, 244.3 g of 2,5-xylenol and 244.3 g of 60% aqueous methanol solution. Further, keeping the temperature at 30° C., 91.11 g of 2,6-dihydroxymethyl-3,4-dimethylphenol obtained above and having purity of 95.4% was added in ten portions over 1 hour. The mixture was stirred at the same temperature for 2 more hours. After completion of the reaction, 50 g of toluene and 500 g of ethyl acetate was added and a phase separation was carried out. Then, metal content was removed by adding 500 g of 1% aqueous oxalic acid solution, followed by stirring the mixture and by carrying out a phase separation. Thereafter, washing with 500 g of deionized water was repeated four times, and the oil phase was concentrated. To the concentrated mass, 500 g of toluene was added and the resulting solution was cooled to 20° C. and filtered. The filter cake was rinsed with 200 g of toluene and dissolved in 500 g of ethyl acetate. The resulting mixture was concentrated. To the concentrated mass, 500 g of toluene was added and the resulting solution was cooled to 20° C. and filtered. The filter cake was rinsed with 200 g of toluene and dried a whole day and night under reduced pressure at 45° C. to obtain 139.8 g of 2,6-bis(4-hydroxy-2,5-dimethylbenzyl)-3,4-dimethylphenol.

Purity (LC): 95.7%
Mass spectrum: MS 390
$^1$H-NMR (dimethylsulfoxide) δ (ppm): 1.88 (s, 6H); 2.01 (s, 3H); 2.06 (s, 3H); 2.08 (s, 3H); 2.27 (s, 3H); 3.70 (s, 2H); 3.80 (s, 2H); 6.17 (s, 1H); 6.48 (s, 1H); 6.59 (s, 2H); 6.68 (s, 1H); 7.85 (s, 1H); 8.80 (s, 1H); 8.88 (s, 1H).

(3) Production of 2,6-bis(4-hydroxy-3-hydroxymethyl-2,5-dimethylbenzyl)- 3,4-dimethylphenol Into a 100 ml four-necked flask were charged 5.86 g of above-obtained 2,6-bis(4-hydroxy-2,5-dimethylbenzyl)-3,4-dimethylphenol having a purity of 95.7%, 2.16 g of sodium hydroxide, 21.6 g of water and 2.16 g of tetrahydrofuran and they were completely dissolved. While stirring at 40° C., 7.30 g of 37% formaldehyde was added dropwise thereto over 1 hour, and the reaction was conducted for one more hour. After completion of reaction, 3 g of 90% aqueous acetic acid solution was added for neutralization, and then the mixture was cooled to 25° C. and filtered. The filter cake was dissolved in a mixed solvent consisting of 100 g of ethyl acetate and 100 g of toluene. The resulting solution was washed with water and the oil phase was concentrated. To the concentrated mass, 100 g of toluene was added, and the mixture was cooled to 20° C., and then filtered. The filter cake was rinsed with 100 g of toluene and dried a whole day and night under reduced pressure at 45° C. to obtain 6.76 g of 2,6-bis(4-hydroxy-3-hydroxymethyl-2,5-dimethylbenzyl)-3,4-dimethylphenol.

Purity (LC): 65%
Mass spectrum: MS 450

(4) Production of 2,6-bis[4-hydroxy-3-(2-hydroxy-5-methylbenzyl)-2,5-dimethylbenzyl]-3,4-dimethylphenol (hereinafter referred to as compound 12)

Into a 100 ml of four-necked flask were charged 0.10 g of para-toluene sulfonic acid, 6.49 g of para-cresol and 6.49 g of toluene. Further, keeping the temperature at 30° C., 2.25 g of above-obtained 2,6-bis(4-hydroxy-3-hydroxymethyl-2,5-dimethylbenzyl)-3,4-dimethylphenol having a purity of 65% was added in ten portions over 1 hour. The mixture was stirred at the same temperature for one more hour. After completion of the reaction, a mixed solvent consisting of 10 g of toluene and 20 g of ethyl acetate was added thereto at 60° C. and further 20 g of deionized water was added. The resulting mixture was stirred and a phase separation was carried out. Then, metal content was removed by adding 20 g of 1% aqueous oxalic acid solution, followed by stirring the mixture and by carrying out a phase separation. Thereafter, washing with 20 g of water was repeated four times, and the oil phase was concentrated. The concentrated mass was subjected to a separation with a silica-gel column chromatography to obtain 0.2 g of compound 12.

Purity (LC): 96.1%
Mass spectrum: MS 630
1H-NMR(dimethylsulfoxide) δ (ppm): 1.88 (s, 3H); 1.90 (s, 3H); 1.97 (s, 3H); 2.04 (s, 9H); 2.13 (s, 3H); 2.15 (s, 3H); 3.78 (s, 2H); 3.83 (s, 2H); 3.88 (s, 2H); 3.90 (m, 2H); 6.14 (s, 1H); 6.35 (s, 1H); 6.40 (s, 2H); 6.69 (m, 2H); 6.70 (s, 1H); 6.74 (m, 2H); 7.87 (s, 1H); 7.91 (s, 1H); 7.96 (s, 1H); 9.22 (s, 1H); 9.26 (s, 1H) (5) Production of quinonediazide sulfonic acid ester of compound 12

Into a 100 ml four-necked flask were charged 0.13 g of compound 12 obtained above, 0.11 g of 1,2-naphthoquinonediazide-5-sulfonyl chloride and 1.20 g of 1,4-dioxane and the temperature was adjusted to 25° C. Thereto, 0.05 g of triethylamine was added dropwise over 1 hour. After addition was completed, the mixture was stirred for 3 hours. Thereafter, 0.02 g of acetic acid was added for neutralization and the reaction mixture was filtered. The filtrate was added to a mixture of 0.1 g of acetic acid and 10 g of deionized water. The resulting mixture was stirred for 1 hour and the precipitated crystalline product was filtered and washed. The finally obtained filter cake was dried a whole day and night at 45° C. under reduced pressure to obtain 0.21 g of the ester (hereinafter referred to as Photosensitizer L).

Mass spectrum of the main component: MS 1094

Synthesis Example 12

(1) Production of 4,4'-methylenebis[2-(2-hydroxy-3-hydroxymethyl-5-methylbenzyl)-3,6-dimethylphenol]

Into a 4 liter four-necked flask were charged 49.66 g of 4,4'-methylenebis[2-(2-hydroxy-5-methylbenzyl)-3,6-dimethylphenol], 9.60 g of sodium hydroxide, 167.1 g of water and 16.7 g of tetrahydrofurane. While stirring at 40° C., 48.7 g of 37% formaldehyde was added dropwise thereto over one hour, and the reaction was conducted for 5 more hours. After completion of the reaction, 19.2 g of 90% aqueous acetic acid solution was added for neutralization, then cooled to 25° C. and filtered. The filtered product thus obtained was rinsed with 100 g of deionized water and dried a whole day and night at 45° C. under reduced pressure to obtain 48.2 g of 4,4'-methylenebis[2-(2-hydroxy-3-hydroxymethyl-5-methylbenzyl)-3,6-dimethylphenol].

Purity measured by liquid chromatography (LC): 84%
Mass spectrum: MS 556
$^1$H-NMR (dimethylsulfoxide) δ (ppm): 1.92 (s, 6H); 2.05 (s, 6H); 2.10 (s, 6H); 3.69 (s, 2H); 3.94 (s, 4H); 4.55 (d, J=7.2 Hz 4H); 5.27 (t, J=7.2 Hz, 2H); 6.27 (s, 2H); 6.60 (s, 2H); 6.85 (s, 2H); 8.06 (s, 2H); 8.45 (s, 2H).

(2) Production of 4,4'-methylenebis[2-{2-hydroxy-3-(2-hydroxy-5-methylbenzyl)-5-methylbenzyl)-3,6-dimethylphenol](hereinafter referred to as compound 13)

Into a 1 liter four-necked flask were charged 1.14 g of para-toluene sulfonic acid, 17.3 g of para-cresol and 34.6 g of toluene. Further, keeping the temperature at 30° C., 11.13 g of 4,4'-methylenebis[2-(2-hydroxy-3-hydroxymethyl-5-methylbenzyl)-3,6-dimethylphenol] obtained above and having a purity of purity of 84% was added in ten portions over and half 1 hour. The mixture was stirred at the same temperature for three more hours. After completion of the reaction, the resulting mixture was filtered and rinsed with 100 g of toluene. The filtered product was added to a mixture of 100 g of toluene and 200 g of ethyl acetate at 60° C. and dissolved completely. Thereafter, 200 g of deionized water was added thereto and the resulting mixture was stirred and a phase separation was carried out. Then, metal content was removed by adding 200 g of 1% aqueous oxalic acid solution, followed by stirring the mixture and by carrying out a phase separation. Thereafter, washing with 200 g of deionized water was repeated four times, and the oil phase was concentrated. To the concentrated mass, 100 g of toluene was added, and the resulting mixture was cooled to 20° C. and filtered. The filter cake was rinsed with 50 g of toluene and dried a whole day and night at 45° C. under reduced pressure to obtain 9.89 g of compound 13.

Purity (LC): 94.7%
Mass spectrum: MS 736
$^1$H-NMR (dimethylsulfoxide) δ (ppm): 1.93 (s, 6H); 1.98 (s, 6H); 2.09 (s, 6H); 2.14 (s, 6H); 3.68 (s, 2H); 3.78 (s, 4H); 3.94 (s, 4H); 6.20 (s, 2H); 6.48 (s, 2H); 6.56 (s, 2H); 6.68 (d, J=7.4 Hz, 2H); 6.80 (m, 4H); 8.05 (brs, 2H); 8.30 (brs, 2H); 9.40 (brs, 2H).

(3) Production of quinonediazide sulfonic acid ester of compound 13

Into a 100 ml four-necked flask were charged 0.37 g of compound 13 obtained above, 0.27 g of 1,2-naphthoquinonediazide-5-sulfonyl chloride and 3.19 g of 1,4-dioxane and the temperature was adjusted to 25° C. Thereto, 0.12 g of triethylamine was added dropwise over 1 hour. After addition was completed, the mixture was stirred for 3 hours. Thereafter, 0.03 g of acetic acid was added for neutralization and the reaction mixture was filtered. The filtrate was added to a mixture of 0.3 g of acetic acid and 30 g of deionized water. The resulting mixture was stirred for 1 hour, filtered and washed. The finally obtained filter cake was dried a whole day and night at 45° C. under reduced pressure to obtain 0.57 g of the ester (hereinafter referred to as Photosensitizer M).

Mass spectrum of the main component: MS 1200 Formula of the compounds 1–13 are shown below.

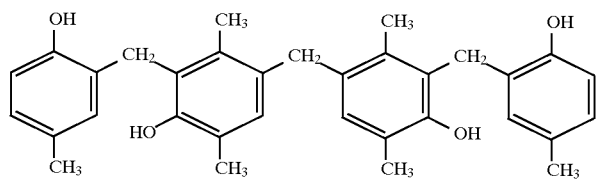

Compound 1

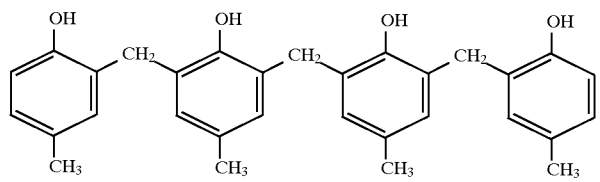

Compound 2

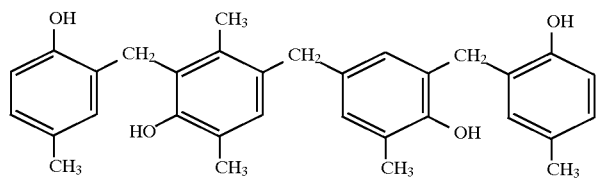

Compound 3

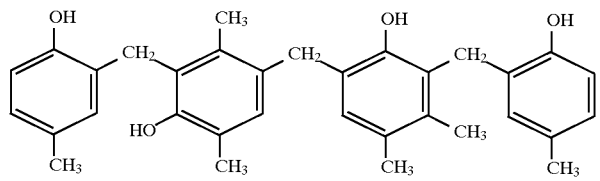

Compound 4

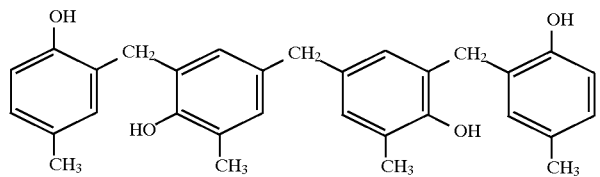

Compound 5

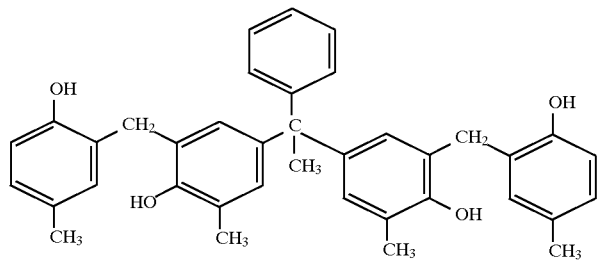

Compound 6

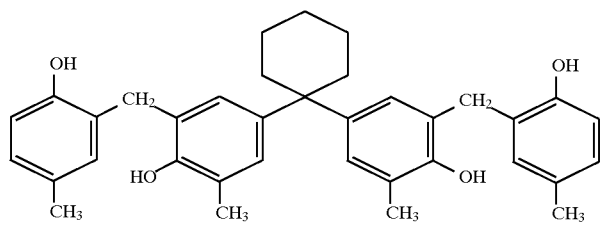

Compound 7

-continued

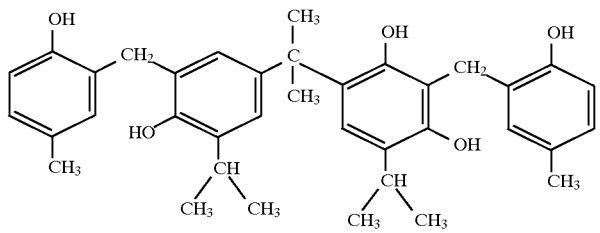
Compound 8

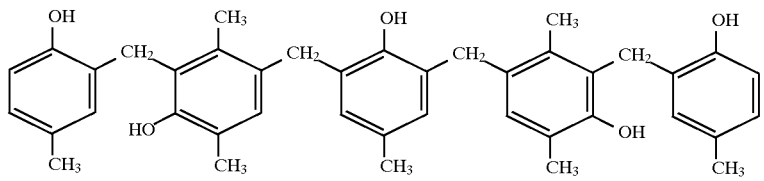
Compound 9

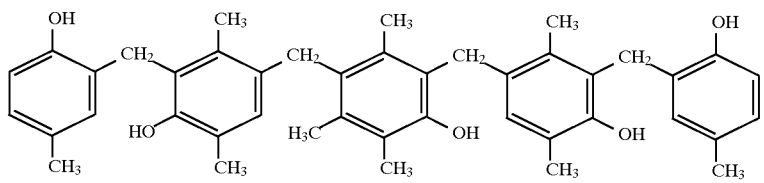
Compound 10

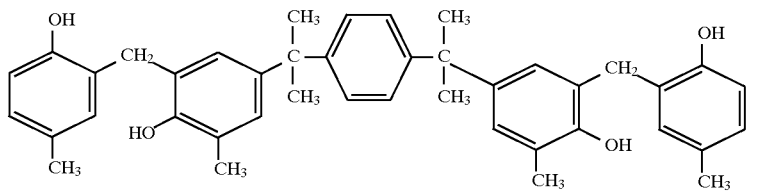
Compound 11

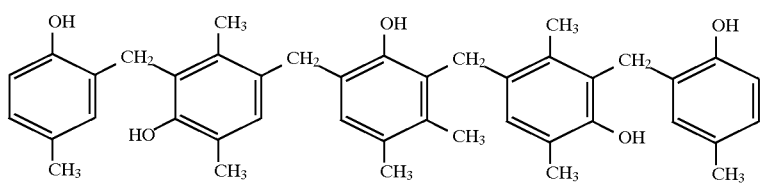
Compound 12

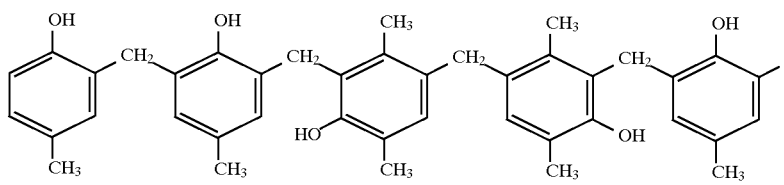
Compound 13

Example 2

(1) Production of 4,4'-methylenebis[2-(4-hydroxy-3-hydroxymethyl-2,5-dimethylbenzyl)-3,6-dimethylphenol]

Into a four-necked flask were charged 78.7 parts of 4,4'-methylenebis[2-(4-hydroxy-2,5-dimethylbenzyl)-3,6-dimethylphenol], 28.8 parts of sodium hydroxide, 850 parts of water and 150 parts of tetrahydrofurane and they were completely dissolved. While stirring at 40° C., 73.0 parts of 37% formaldehyde was added dropwise thereto and the reaction was conducted for 6 hours. After completion of the reaction, 45.0 parts of acetic acid was added for neutralization and then the mixture was cooled to 25° C. Thereafter, the precipitated crystalline product was filtered out and rinsed with 1000 parts of deionized water. The filtered product was dried a whole day and night under reduced pressure at 45° C. to obtain 71.9 parts of 4,4'-methylenebis[2-(4-hydroxy-3-hydroxymethyl-2,5-dimethylbenzyl)-3,6-dimethylphenol]

(2) Production of 4,4'-methylenebis[2-{4-hydroxy-3-(2-hydroxy-5-methylbenzyl)-2,5-dimethylbenzyl}-3,6-dimethylphenol](hereinafter referred to as compound 14)

Into a four-necked flask were charged 3.80 parts of para-toluene sulfonic acid, 108.1 parts of para-cresol and 216 parts of toluene. Further, keeping the temperature at 40° C., 58.5 parts of 4,4'-methylenebis[2-(4-hydroxy-3-hydroxymethyl-2,5-dimethylbenzyl)- 3,6-dimethylphenol] obtained above was added. The mixture was stirred at the same temperature for three more hours. After completion of the reaction, the mixture was cooled to 20° C. and filtered, and the filter cake was rinsed with 400 parts of toluene. The filter cake was added to a mixed solvent of 400 parts of toluene and 600 parts of ethyl acetate and dissolved at 60° C. Thereafter, 400 parts of deionized water was added thereto and the resulting mixture was stirred and a phase separation was carried out. Thereafter, washing with 400 parts of deionized water was repeated four times, and the oil phase was concentrated. To the concentrated mass, 400 parts of toluene was added and the resulting solution was cooled to 20° C. and filtered. The filter cake was rinsed with 200 parts of toluene and dried a whole day and night under reduced pressure at 45° C. to obtain 26.9 parts of compound 14.

Mass spectrum: MS 764

$^1$H-NMR (dimethylsulfoxide) δ (ppm): 1.88 (s, 6H); 1.98 (s, 6H); 2.03 (s, 6H); 2.10 (s, 6H); 2.12 (s, 6H); 3.71 (s, 4H); 3.83 (s, 4H); 3.90 (s, 4H); 6.14 (s, 2H); 6.40 (s, 2H); 6.53 (s, 2H); 6.70 (d, J=8.2 Hz, 2H); 6.75 (d, J=8.1 Hz, 2H).

(3) Production of quinonediazide sulfonic acid ester of compound

Into a four-necked flask were charged 7.7 parts of compound 14 obtained above, 5.4 parts of 1,2-naphthoquinonediazide-5-sulfonyl chloride and 65 parts of 1,4-dioxane and the temperature was adjusted to 25° C. Thereto, 2.4 parts of triethylamine was added dropwise. After addition was completed, the mixture was stirred for 3 hours. Thereafter, 0.6 part of acetic acid was added for neutralization and the reaction mixture was filtered. The filtrate was added to 770 parts of 1% aqueous acetic acid solution. The resulting mixture was stirred for 1 hour, filtered and washed with deionized water. The finally obtained filter cake was dried a whole day and night at 45° C. under reduced pressure to obtain 10.7 parts of the ester (hereinafter referred to as Photosensitizer N).

Mass spectrum of the main component: MS 1228

Example 3

(1) Production of 2,6-bis(4-hydroxy-3-hydroxymethyl-5-methylbenzyl)-3,4-dimethylphenol Into a four-necked flask were charged 54.4 parts of 2,6-bis(4-hydroxy-3-methylbenzyl)-3,4-dimethylphenol, 21.6 parts of sodium hydroxide, 900 parts of water and 100 parts of tetrahydrofurane and they were completely dissolved. While stirring at 40° C., 73.0 parts of 37% formaldehyde was added dropwise thereto and the reaction was conducted for 6 hours. After completion of the reaction, 36.0 parts of acetic acid was added for neutralization and then the mixture was cooled to 25° C. Thereafter, the precipitated crystalline product was filtered out and rinsed with 1000 parts of deionized water. The filtered product was dried a whole day and night under reduced pressure at 45° C. to obtain 57.1 parts of 2,6-bis(4-hydroxy-3-hydroxymethyl-5-methylbenzyl)-3,4-dimethylphenol.

(2) Production of 2,6-bis[4-hydroxy-3-(2-hydroxy-5-methylbenzyl)-5-methylbenzyl]-3,4-dimethylphenol (hereinafter referred to as compound 15)

Into a four-necked flask were charged 3.80 parts of para-toluene sulfonic acid, 108.1 parts of para-cresol and 216 parts of toluene. Further, keeping the temperature at 40° C., 42.3 parts of 2,6-bis(4-hydroxy-3-hydroxymethyl-5-methylbenzyl)-3,4-dimethylphenol obtained above was added. The mixture was stirred at the same temperature for three more hours. After completion of the reaction, the mixture was cooled to 20° C. and filtered, and the filter cake was rinsed with 400 parts of toluene. The filter cake was added to a mixed solvent of 400 parts of toluene and 600 parts of ethyl acetate and dissolved at 60° C. Thereafter, 400 parts of deionized water was added thereto and the resulting mixture was stirred and a phase separation was carried out. Thereafter, washing with 400 parts of deionized water was repeated four times, and the oil phase was concentrated. To the concentrated mass, 400 parts of toluene was added and the resulting solution was cooled to 20° C. and filtered. The filter cake was rinsed with 200 parts of toluene and dried a whole day and night under reduced pressure at 45° C. to obtain 25.6 parts of compound 15.

Mass spectrum: MS 602

$^1$H-NMR (dimethylsulfoxide) δ (ppm): 1.95 (s, 3H); 2.02 (s, 3H); 2.06 (s, 3H); 2.07 (s, 3H); 2.10 (s, 6H); 3.70 (s, 2H); 3.72 (s, 2H); 3.75 (s, 2H); 3.83 (s, 2H); 6.56 (s, 1H); 6.60 (s, 1H); 6.69 (m, 5H); 6.76 (m, 4H); 7.69 (s, 1H); 7.88 (brs, 2H); 9.12 (brs, 2H).

(3) Production of quinonediazide sulfonic acid ester of compound 15

Into a four-necked flask were charged 6.0 parts of compound 15 obtained above, 5.4 parts of 1,2-naphthoquinonediazide-5-sulfonyl chloride and 57 parts of 1,4-dioxane and the temperature was adjusted to 25° C. Thereto, 2.4 parts of triethylamine was added dropwise. After addition was completed, the mixture was stirred for 3 hours. Thereafter, 0.6 part of acetic acid was added for neutralization and the reaction mixture was filtered. The filtrate was added to 780 parts of 1% aqueous acetic acid solution. The resulting mixture was stirred for 1 hour, filtered and washed with deionized water. The finally obtained filter cake was dried a whole day and night at 45° C. under reduced pressure to obtain 10.6 parts of the ester (hereinafter referred to as Photosensitizer O).

Mass spectrum of the main component: MS 1066

Example 4

(1) Production of 2,6-bis(4-hydroxy-3-hydroxymethyl-5-methylbenzyl)-4-methylphenol Into a four-necked flask were charged 52.3 parts of 2,6-bis(4-hydroxy-3-methylbenzyl)-4-methylphenol, 21.6 parts of sodium hydroxide, 900 parts of water and 100 parts of tetrahydrofurane and they were completely dissolved. While stirring at 40° C., 73.0 parts of 37% formaldehyde was added dropwise thereto and the reaction was conducted for 6 hours. After completion of the reaction, 36.0 parts of acetic acid was added for neutralization and then the mixture was cooled to 25° C. Thereafter, the precipitated crystalline product was filtered out and rinsed with 1000 parts of deionized water. The filtered product was dried a whole day and night under reduced pressure at 45° C. to obtain 55.1 parts of 2,6-bis(4-hydroxy-3-hydroxymethyl-5-methylbenzyl)-4-methylphenol.

(2) Production of 2,6-bis[4-hydroxy-3-(2-hydroxy-5-methylbenzyl)-5-methylbenzyl]-4-methylphenol (hereinafter referred to as compound 16)

Into a four-necked flask were charged 3.8 parts of para-toluene sulfonic acid, 108.1 parts of para-cresol and 216 parts of toluene. Further, keeping the temperature at 40° C., 40.8 parts of 2,6-bis(4-hydroxy-3-hydroxymethyl-5-methylbenzyl)-4-methylphenol obtained above was added. The mixture was stirred at the same temperature for three more hours. After completion of the reaction, the mixture was cooled to 20° C. and filtered, and the filter cake was rinsed with 400 parts of toluene. The filter cake was added to a mixed solvent of 400 parts of toluene and 600 parts of ethyl acetate and dissolved at 60° C. Thereafter, 400 parts of deionized water was added thereto and the resulting mixture was stirred and a phase separation was carried out. Thereafter, washing with 400 parts of deionized water was repeated four times, and the oil phase was concentrated. To the concentrated mass, 400 parts of toluene was added and the resulting solution was cooled to 20° C. and filtered. The filter cake was rinsed with 200 parts of toluene and dried a whole day and night under reduced pressure at 45° C. to obtain 24.5 parts of compound 16.

Mass spectrum: MS 588

$^1$H-NMR (dimethylsulfoxide) δ (ppm): 2.02 (s, 3H); 2.10 (s, 12H); 3.68 (s, 4H); 3.74 (s, 4H); 6.51 (s, 2H); 6.68 (d, J=7.9 Hz, 2H); 6.70 (s, 2H); 6.74 (s, 4H); 6.78 (d, J=7.9 Hz, 2H); 8.01 (s, 1H); 8.07 (brs, 2H); 9.37 (brs, 2H).
(3) Production of quinonediazide sulfonic acid ester of compound 16

Into a four-necked flask were charged 5.9 parts of compound 16 obtained above, 5.4 parts of 1,2-naphthoquinonediazide-5-sulfonyl chloride and 56 parts of 1,4-dioxane and the temperature was adjusted to 25° C. Thereto, 2.4 parts of triethylamine was added dropwise. After addition was completed, the mixture was stirred for 3 hours. Thereafter, 0.6 part of acetic acid was added for neutralization and the reaction mixture was filtered. The filtrate was added to 780 parts of 1% aqueous acetic acid solution. The resulting mixture was stirred for 1 hour, filtered and washed with deionized water. The finally obtained filter cake was dried a whole day and night at 45° C. under reduced pressure to obtain 10.5 parts of the ester (hereinafter referred to as Photosensitizer P).

Mass spectrum of the main component: MS 1052

Example 5

(1) Production of 2,6-bis(4-hydroxy-3-hydroxymethyl-2,5,6-trimethylbenzyl)-4-methylphenol Into a four-necked flask were charged 60.7 parts of 2,6-bis(4-hydroxy-2,5,6-trimethylbenzyl)-4-methylphenol, 21.6 parts of sodium hydroxide, 900 parts of water and 100 parts of tetrahydrofurane and they were completely dissolved. While stirring at 40° C., 73.0 parts of 37% formaldehyde was added dropwise thereto and the reaction was conducted for 6 hours. After completion of the reaction, 36.0 parts of acetic acid was added for neutralization and then the mixture was cooled to 25° C. Thereafter, the precipitated crystalline product was filtered out and rinsed with 1000 parts of deionized water. The filtered product was dried a whole day and night under reduced pressure at 45° C. to obtain 65.6 parts of 2,6-bis(4-hydroxy-3-hydroxymethyl-2,5,6-trimethylbenzyl)-4-methylphenol.

(2) Production of 2,6-bis[4-hydroxy-3-(2-hydroxy-5-methylbenzyl)-2,5,6-trimethylbenzyl ]-4-methylphenol (hereinafter referred to as compound 17)

Into a four-necked flask were charged 3.8 parts of para-toluene sulfonic acid, 108.1 parts of para-cresol and 324 parts of toluene. Further, keeping the temperature at 40° C., 46.5 parts of 2,6-bis(4-hydroxy-3-hydroxymethyl-2,5,6-trimethylbenzyl)-4-methylphenol obtained above was added. The mixture was stirred at the same temperature for 3 more hours. After completion of the reaction, the mixture was cooled to 20° C. and filtered, and the filter cake was rinsed with 400 parts of toluene. The filter cake was added to a mixed solvent of 400 parts of toluene and 600 parts of ethyl acetate and dissolved at 60° C. Thereafter, 400 parts of deionized water was added there to and the resulting mixture was stirred and a phase separation was carried out. Thereafter, washing with 400 parts of deionized water was repeated four times, and the oil phase was concentrated. To the concentrated mass, 400 parts of toluene was added and the resulting solution was cooled to 20° C. and filtered. The filter cake was rinsed with 200 parts of toluene and dried a whole day and night under reduced pressure at 45° C. to obtain 23.3 parts of compound 17.

Mass spectrum: MS 644

$^1$H-NMR (dimethylsulfoxide) δ (ppm): 1.85 (s, 3H); 1.88 (s, 6H); 2.01 (s, 6H); 2.03 (s, 6H); 2.14 (s, 6H); 3.88 (s, 8H); 5.99 (s, 2H); 6.31 (s, 2H); 6.67 (d, J=7.6 Hz, 2H); 6.74 (d, J=7.6 Hz, 2H); 7.87 (s, 2H); 8.31 (s, 1H); 9.21 (s, 2H).

(3) Production of quinonediazide sulfonic acid ester of compound 17

Into a four-necked flask were charged 6.4 parts of compound 17 obtained above, 5.4 parts of 1,2-naphthoquinonediazide-5-sulfonyl chloride and 59 parts of 1,4-dioxane and the temperature was adjusted to 25° C. Thereto, 2.4 parts of triethylamine was added dropwise. After addition was completed, the mixture was stirred for 3 hours. Thereafter, 0.6 part of acetic acid was added for neutralization and the reaction mixture was filtered. The filtrate was added to 780 parts of 1% aqueous acetic acid solution. The resulting mixture was stirred for 1 hour, filtered and washed with deionized water. The finally obtained filter cake was dried a whole day and night at 45° C. under reduced pressure to obtain 10.8 parts of the ester (hereinafter referred to as Photosensitizer Q).

Mass spectrum of the main component: MS 1108

Example 6

(1) Production of 2,4-bis(4-hydroxy-3-hydroxymethyl-2,5-dimethylbenzyl)-3,6-dimethylphenol Into a four-necked flask were charged 58.6 parts of 2,4-bis(4-hydroxy-2,5-dimethylbenzyl)-3,6-dimethylphenol, 21.6 parts of sodium hydroxide, 900 parts of water and 100 parts of tetrahydrofurane and they were completely dissolved. While stirring at 40° C., 73.0 parts of 37% formaldehyde was added dropwise thereto and the reaction was conducted for 6 hours. After completion of the reaction, 36.0 parts of acetic acid was added for neutralization and then the mixture was cooled to 25° C. Thereafter, the precipitated crystalline product was filtered out and rinsed with 1000 parts of deionized water. The filtered product was dried a whole day and night under reduced pressure at 45° C. to obtain 59.5 parts of 2,4-bis(4-hydroxy-3-hydroxymethyl-2,5-dimethylbenzyl)-3,6-dimethylphenol.

(2) Production of 2,4-bis[4-hydroxy-3-(2-hydroxy-5-methylbenzyl)-2,5-dimethylbenzyl]-3,6-dimethylphenol (hereinafter referred to as compound 18)

Into a four-necked flask were charged 3.8 parts of para-toluene sulfonic acid, 108.1 parts of para-cresol and 216 parts of toluene. Further, keeping the temperature at 40° C., 45.1 parts of 2,4-bis(4-hydroxy-3-hydroxymethyl-2,5-dimethylbenzyl)-3,6-dimethylphenol obtained above was added. The mixture was stirred at the same temperature for 3 more hours. After completion of the reaction, the mixture was cooled to 20° C. and filtered, and the filter cake was rinsed with 400 parts of toluene. The filter cake was added to a mixed solvent of 400 parts of toluene and 600 parts of ethyl acetate and dissolved at 60° C. Thereafter, 400 parts of deionized water was added thereto and the resulting mixture was stirred and a phase separation was carried out. Thereafter, washing with 400 parts of deionized water was repeated four times, and the oil phase was concentrated. To the concentrated mass, 400 parts of toluene was added and the resulting solution was cooled to 20° C. and filtered. The filter cake was rinsed with 200 parts of toluene and dried a whole day and night under reduced pressure at 45° C. to obtain 20.8 parts of compound 18.

Mass spectrum: MS 630

$^1$H-NMR (dimethylsulfoxide) δ (ppm): 1.86 (s, 3H); 1.93 (s, 3H); 1.98 (s, 3H); 2.02 (s, 6H); 2.09 (s, 3H); 2.10 (s, 3H); 2.11 (s, 3H); 3.69 (s, 2H); 3.82 (s, 2H); 3.88 (s, 2H); 3.89 (s, 2H); 6.13 (s, 1H); 6.33 (s, 1H); 6.39 (s, 1H); 6.47 (s, 1H); 6.53 (s, 1H); 6.69 (d, J=8.1 Hz, 2H); 6.75 (d, J=8.1 Hz, 2H); 7.86 (s, 1H); 7.87 (s, 1H); 7.93 (s, 1H); 9.23 (s, 1H); 9.25 (s, 1H);

(3) Production of quinonediazide sulfonic acid ester of compound 18

Into a four-necked flask were charged 6.3 parts of compound 18 obtained above, 5.4 parts of 1,2-naphthoquinonediazide-5-sulfonyl chloride and 58.5 parts of 1,4-dioxane and the temperature was adjusted to 25° C. Thereto, 2.4 parts of triethylamine was added dropwise. After addition was completed, the mixture was stirred for 3 hours. Thereafter, 0.6 part of acetic acid was added for neutralization and the reaction mixture was filtered. The filtrate was added to 780 parts of 1% aqueous acetic acid solution. The resulting mixture was stirred for 1 hour, filtered and washed with deionized water. The finally obtained filter cake was dried a whole day and night at 45° C. under reduced pressure to obtain 10.4 parts of the ester (hereinafter referred to as Photosensitizer R).

Mass spectrum of the main component: MS 1094

Example 7

(1) Production of 2,4-bis(4-hydroxy-3-hydroxymethyl-5-methylbenzyl)-3,6-dimethylphenol Into a four-necked flask were charged 54.4 parts of 2,4-bis(4-hydroxy-3-methylbenzyl)-3,6-dimethylphenol, 21.6 parts of sodium hydroxide, 900 parts of water and 100 parts of tetrahydrofurane and they were completely dissolved. While stirring at 40° C., 73.0 parts of 37% formaldehyde was added dropwise thereto and the reaction was conducted for 6 hours. After completion of the reaction, 36.0 parts of acetic acid was added for neutralization and then the mixture was cooled to 25° C. Thereafter,the precipitated crystalline product was filtered out and rinsed with 1000 parts of deionized water. The filtered product was dried a whole day and night under reduced pressure at 45° C. to obtain 56.4 parts of 2,4-bis(4-hydroxy-3-hydroxymethyl-5-methylbenzyl)-3,6-dimethylphenol.

(2) Production of 2,4-bis[4-hydroxy-3-(2-hydroxy-5-methylbenzyl)-5-methylbenzyl]-3,6-dimethylphenol (hereinafter referred to as compound 19)

Into a four-necked flask were charged 3.8 parts of para-toluene sulfonic acid, 108.1 parts of para-cresol and 216 parts of toluene. Further, keeping the temperature at 40° C., 42.3 parts of 2,4-bis(4-hydroxy-3-hydroxymethyl-5-methylbenzyl)-3,6-dimethylphenol obtained above was added. The mixture was stirred at the same temperature for 3 more hours. After completion of the reaction, the mixture was cooled to 20° C. and filtered, and the filter cake was rinsed with 400 parts of toluene. The filter cake was added to a mixed solvent of 400 parts of toluene and 600 parts of ethyl acetate and dissolved at 60° C. Thereafter, 400 parts of deionized water was added thereto and the resulting mixture was stirred and a phase separation was carried out. Thereafter, washing with 400 parts of deionized water was repeated four times, and the oil phase was concentrated. To the concentrated mass, 400 parts of toluene was added and the resulting solution was cooled to 20° C. and filtered. The filter cake was rinsed with 200 parts of toluene and dried a whole day and night under reduced pressure at 45° C. to obtain 18.1 parts of compound 19.

Mass spectrum: MS 602

$^1$H-NMR (dimethylsulfoxide) δ (ppm): 1.91 (s, 3H); 1.99 (s, 3H); 2.04 (s, 3H); 2.07 (s, 3H); 2.08 (s, 3H); 2.10 (s, 3H); 3.61 (s, 2H); 3.70 (s, 2H); 3.71 (s, 2H); 3.80 (s, 2H); 6.55 (s, 2H); 6.65 (d, J=8.2 Hz, 2H); 6.66 (s, 2H); 6.69 (s, 4H); 6.78 (d, J=8.2 Hz, 2H); 7.89 (s, 1H); 8.02 (brs, 2H); 9.34 (brs, 2H).

(3) Production of quinonediazide sulfonic acid ester of compound 19

Into a four-necked flask were charged 6.0 parts of compound 19 obtained above, 5.4 parts of 1,2-naphthoquinonediazide-5-sulfonyl chloride and 57 parts of 1,4-dioxane and the temperature was adjusted to 25° C. Thereto, 2.4 parts of triethylamine was added dropwise. After addition was completed, the mixture was stirred for 3 hours. Thereafter, 0.6 part of acetic acid was added for neutralization and the reaction mixture was filtered. The filtrate was added to 780 parts of 1% aqueous acetic acid solution. The resulting mixture was stirred for 1 hour, filtered and washed with deionized water. The finally obtained filter cake was dried a whole day and night at 45° C. under reduced pressure to obtain 10.2 parts of the ester (hereinafter referred to as Photosensitizer S).

Mass spectrum of the main component: MS 1066

Reference Example

Production of novolak resin

Into a 1000 ml four-necked flask were charged 148.5 g of meta-cresol, 121.5 g of para-cresol, 252 g of methyl isobutyl ketone, 37.0 g of 10% oxalic acid and 84.8 g of 90% aqueous acetic acid solution. Heating the mixture in an oil bath at 100° C. with stirring, 129.5 g of 37% formaldehyde solution was added dropwise thereto over 40 minutes and reaction was effected for further 15 hours. Then, the mixture was washed with water and water was removed to obtain 466 g of a methyl isobutyl ketone solution containing 42.3% of novolak resin. The resin had a weight average molecular weight, converted into polystyrene, of 4300 as determined by GPC.

Into a 5 litter bottom-discharging separable flask was charged 450 g of the above obtained solution and 909.6 g of methyl isobutyl ketone and 996.1 g of n-heptane were added thereto. After stirring at 60° C. for 30 minutes, the mixture was left still and subjected to a phase-separation. To the lower layer mass obtained by the separation was added 380 g of 2-heptanone, and methyl isobutyl ketone and n-heptane were removed therefrom by an evaporator to obtain a 2-heptanone solution of a novolak resin. The resin had a weight average molecular weight, converted into polystyrene, of 9000 as determined by GPC, and a ratio of an area for a portion having a molecular weight converted into polystyrene of 900 or less was 14% based on the total area in the pattern.

Examples 8–26

A 15 parts portion, converted into solid weight, of a solution of the novolak resin in 2-heptanone obtained in Reference Example, 3.9 parts of 1,3-bis[1-(2,4-dihydroxyphenyl)-1-methylethyl]benzene as an additive, 5 parts of Photosensitizer shown in Table 1, 1 part of a condensation product, in a molar ratio of 1:4, of 1,2,3-trihydroxy-4-(4-hydroxy-2,5-dimethylbenzyl)benzene and 1,2-naphthoquinone-diazide-5-sulfonylchloride, as the other photosensitizer, and 2-heptanone were mixed in such manner that the total amount of 2- heptanone became 50 parts and they were dissolved. The solution was filtered through a fluorine resin filter having a pore size of 0.2 μm to give a resist solution.

The above resist solution was coated onto silicone wafers, using a spin coator so that the resist film thickness after dried become 1.1 μm, and the wafers were washed by conventional means and were baked on a hot plate at 90° C. for 1 minute. Then, they were exposed to irradiation with a reduced projection exposing machine (manufactured by Nikon Kabushiki Kaisha, NSR 1755i 7A, NA=0.5) having an exposing wave length of 365 nm (i-line) changing the exposure amount in steps. Then, the wafers were baked on a hot plate at 110° C. for 1 minute and developed with a developing solution "SOPD" (manufactured by Sumitomo Chemical Company, Limited) for 1 minute to give positive patterns. Each of the positive patterns were evaluated in the following manner. The results are shown in Table 1.

Effective sensitivity: This was expressed in terms of the exposure amount at which the 0.50 μm line and space pattern became 1:1.

Resolution: The size of the line and space pattern separable without loss of film was measured with a scanning electron microscope at an exposure amount at which the line and space pattern became 1:1 (effective sensitivity).

Profile: The shape of cross-section of 0.45 μm line and space pattern at the effective sensitivity was observed with a scanning electron microscope.

Focus (Depth of focus): The depth of focus where 0.40 μm line and space pattern was separable without loss of film at the effective sensitivity was measured with a scanning electron microscope.

Scum: Presence or absence of scum (undeveloped residue) was observed with a scanning electron microscope.

γ-value: The ascent θ of a line obtained by plotting normalized thickness of resist film (=residual thickness of resist film/original thickness of resist film) with respect to the logarithm of exposure amount was measured and tan θ was taken as the γ-value.

TABLE 1

| Example No. | Photo-sensitizer | Effective Sensitivity msec | Resolution μm | Depth of Focus μm | Scum | γ-value |
|---|---|---|---|---|---|---|
| 8 | A | 300 | 0.32 | 1.5 | none | 7.62 |
| 9 | B | 400 | 0.35 | 1.5 | none | 6.92 |
| 10 | C | 210 | 0.375 | 1.6 | none | 7.12 |
| 11 | D | 390 | 0.35 | 1.6 | none | 8.92 |
| 12 | E | 170 | 0.375 | 1.5 | none | 5.92 |
| 13 | F | 300 | 0.35 | 1.6 | none | 6.92 |

TABLE 1-continued

| Example No. | Photo-sensitizer | Effective Sensitivity msec | Resolution μm | Depth of Focus μm | Scum | γ-value |
|---|---|---|---|---|---|---|
| 14 | G | 340 | 0.375 | 1.5 | none | 5.68 |
| 15 | H | 440 | 0.35 | 1.5 | none | 6.98 |
| 16 | I | 230 | 0.375 | 1.5 | none | 6.82 |
| 17 | J | 250 | 0.35 | 1.5 | none | 7.61 |
| 18 | K | 320 | 0.375 | 1.5 | none | 7.12 |
| 19 | L | 240 | 0.375 | 1.5 | none | 6.92 |
| 20 | M | 380 | 0.375 | 1.5 | none | 5.92 |
| 21 | N | 420 | 0.34 | — | none | 5.43 |
| 22 | O | 130 | 0.35 | — | none | 3.39 |
| 23 | P | 112 | 0.39 | — | none | 4.11 |
| 24 | Q | 167 | 0.32 | — | none | 4.53 |
| 25 | R | 198 | 0.34 | — | none | 4.06 |
| 26 | S | 142 | 0.37 | — | none | 3.71 |

Profile in Example 21–26

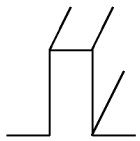

The naphthoquinonediazide sulfonic acid ester of polyphenol compounds of the present invention are useful as a photosensitizer for a photosensitive resin composition. The positive photo resist of the present invention is well balanced among various properties as the resist for minute processing of semiconductors such as high sensitivity, high resolution (γ-value), high heat resistance, good profile, good focus allowance, little development residue and the like.

What we claim is:

1. A phenol compound represented by the following formula VII.

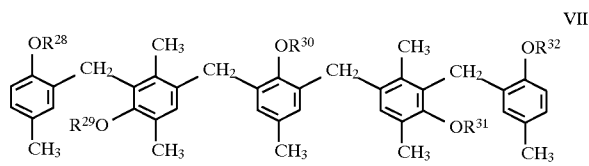

wherein $R^{28}$, $R^{29}$, $R^{30}$, $R^{31}$ and $R^{32}$ independently represent hydrogen, 1,2-naphthoquinonediazide-4-sulfonyl or 1,2-naphthoquinonediazide-5-sulfonyl.

2. A phenol compound represented by the following formula X.

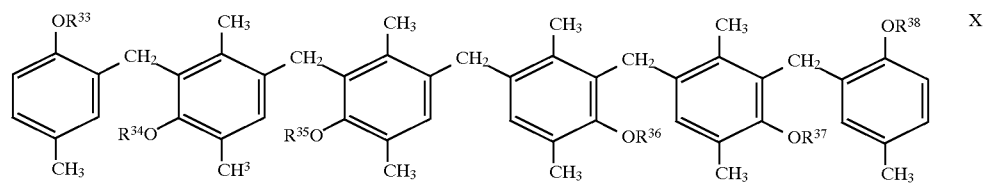

wherein $R^{33}$, $R^{34}$, $R^{35}$, $R^{36}$, $R^{37}$ and $R^{38}$ independently represent hydrogen, 1,2-naphthoquinonediazide-4-sulfonyl or 1,2-naphthoquinonediazide-5-sulfonyl.

3. A phenol compound represented by the following formula XI.

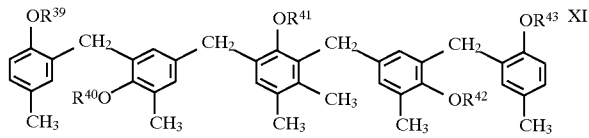

wherein $R^{39}$, $R^{40}$, $R^{41}$, $R^{42}$ and $R^{43}$ independently represent hydrogen, 1,2-naphthoquinonediazide-4-sulfonyl or 1,2-naphthoquinonediazide-5-sulfonyl.

4. A phenol compound represented by the following formula XIII:

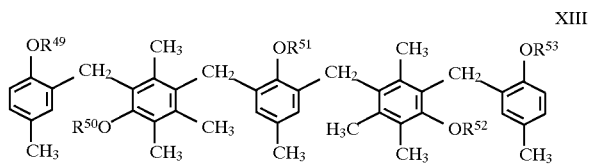

wherein $R^{49}$, $R^{50}$, $R^{51}$, $R^{52}$ and $R^{53}$ independently represent hydrogen, 1,2-naphthoquinonediazide-4-sulfonyl or 1,2-naphthoquinonediazide-5-sulfonyl.

5. A phenol compound represented by the following formula XIV:

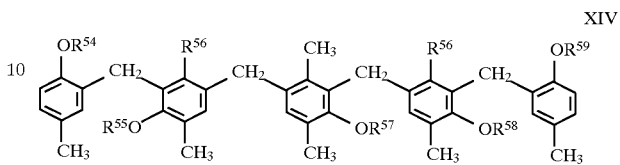

wherein $R^{56}$ represents hydrogen or methyl and $R^{54}$, $R^{55}$, $R^{57}$, $R^{58}$ and $R^{59}$ independently represent hydrogen, 1,2-naphthoquinonediazide-4-sulfonyl or 1,2-naphthoquinonediazide-5-sulfonyl.

6. 2,6-Bis(4-hydroxy-3-hydroxymethyl-2,5-dimethylbenzyl)-4-methylphenol.

* * * * *